United States Patent
Chapman et al.

(10) Patent No.: US 7,011,948 B2
(45) Date of Patent: *Mar. 14, 2006

(54) DETECTION OF LIGAND-ANTILIGAND COMPLEX FORMATION BY ELECTROMAGNETICALLY DETECTABLE BULK PROPERTY MEASUREMENT

(75) Inventors: Robert G. Chapman, Burlingame, CA (US); Pejman Ghanouni, Menlo Park, CA (US); Igor Shmulevich, San Ramon, CA (US); David Balaban, San Jose, CA (US); Joseph A. Heanue, Halfmoon Bay, CA (US); Andrew P. May, San Francisco, CA (US); Nikolai Sharkov, San Francisco, CA (US)

(73) Assignee: MDS Sciex, South San Francisco, CA (US)

(*) Notice: Subject to any disclaimer, the term of this patent is extended or adjusted under 35 U.S.C. 154(b) by 574 days.

This patent is subject to a terminal disclaimer.

(21) Appl. No.: 10/198,465

(22) Filed: Jul. 17, 2002

(65) Prior Publication Data

US 2004/0014045 A1    Jan. 22, 2004

(51) Int. Cl.
*C12Q 1/68* (2006.01)
*C12P 19/34* (2006.01)
*G01N 15/06* (2006.01)
*G01N 33/00* (2006.01)
*B01L 3/00* (2006.01)

(52) U.S. Cl. .................... 435/6; 435/7.1; 435/7.21; 435/4; 435/287.2; 435/288.7; 436/501; 436/518; 436/524; 436/527; 436/528; 436/535; 422/68.1; 422/81; 422/99

(58) Field of Classification Search ............ 435/6, 435/7.1, 7.21, 4, 287.2, 288.7, 808; 436/501, 436/518, 524, 527, 528, 535; 422/68.1, 81
See application file for complete search history.

(56) References Cited

U.S. PATENT DOCUMENTS 5,363,052 A   11/1994   McKee
5,656,428 A   8/1997    McAllister et al.
6,048,692 A   4/2000    Maracas et al.

FOREIGN PATENT DOCUMENTS

EP    0519250    12/1992

OTHER PUBLICATIONS

Lieb, Simplex Method of Nonlinear Least Squares- A Logical Complementary Method to Linear Least Squares Analysis of Dat Aug. 1997, Journal of Chemical Education, vol. 74, No. 8, p. 1008.*
Malmqvist et al., "Biomolecular interaction analysis: affinity biosensor technologies for functional analysis of proteins" 1997, Curent Opinion in Chemical Biology, 1:378-383.*
McKee et al., "Real-time chemical sensing of aqueous ethanol glucose mixtures", IEEE Transactions on Instrumentation and Measurement, 49(1):114-119 (2000).
Stuchly et al., "Coaxial line reflection methods for measuring dielectric properties of biological substances at radio and microwave frequencies—A review", IEEE Transactions on Instrumentation and Measurement, vol. IM-29, No. 3, Sep. 1980, pp. 176-183.

* cited by examiner

*Primary Examiner*—Kenneth R. Horlick
*Assistant Examiner*—Joyce Tung
(74) *Attorney, Agent, or Firm*—Kelvan Patrick Howard; Richard Neeley

(57) ABSTRACT

Disclosed are methods for analyzing molecular binding events in which the formation of ligand/antiligand complexes can be directly detected in a mixture without requiring separation of the components of the mixture from each other by measuring bulk properties of the mixture (i.e., properties that have contributions from several or all of the components present in the mixture). Using these techniques, it is possible to screen libraries without labeling either the target antiligand or ligand. The invention also provides a method for determining the strength of ligand/antiligand binding by further analysis of the same signals.

14 Claims, 18 Drawing Sheets

+

=

+

=

DETECTION OF LIGAND-ANTILIGAND COMPLEX FORMATION BY ELECTROMAGNETICALLY DETECTABLE BULK PROPERTY MEASUREMENT

BACKGROUND OF THE INVENTION

1. Field of the Invention

The present invention broadly relates to methods for detecting binding interactions between various types of ligands and antiligands, in particular label-free detection of ligand/antiligand complex formation in a mixture without requiring separation of the components of the mixture from each other. In one implementation, the present invention relates to methods for screening ligands for those having binding affinity for an antiligand protein or biological-cell target of interest. As such, the present invention is useful within the fields of fundamental biomedical and biochemical research, especially drug discovery and medical diagnostics.

2. Description of Related Art

Proteins play a variety of key roles in biological processes and functions, including for example, functioning as catalysts, regulators of biochemical pathways, receptors, and as important elements in immune response. Given their diverse and important roles, it is not surprising that pharmaceutical researchers have viewed ligands that bind to proteins as attractive candidates for therapeutic agents. One traditional approach for drug discovery simply involved making modifications to natural regulators. As more data regarding structure function relationships became available, it became possible to engage in rational drug design using computers and x-ray structures to aid in synthesizing molecules tailored to fit the active site of an enzyme, for example. However, even using such advanced techniques, drug screening and development remained an often tedious and time-consuming process.

More recent drug discovery methods take a different approach and involve screening extremely large libraries of compounds for their ability to bind protein targets of interest. This type of approach typically begins with the identification of a potential protein target, such as a receptor. A diverse library is then prepared containing ligands to be screened for their ability to bind the target. The libraries can be random peptide libraries, carbohydrate libraries, natural product libraries, synthetic compound libraries, etc. Often the libraries are prepared using recently developed combinatorial techniques. These libraries are subsequently subjected to high throughput screening to identify ligands that bind to the target. Because the key feature of this approach is to screen a huge number of molecules, the success of this approach hinges on the ability to rapidly screen and identify ligands that do bind the target. Ligands initially identified as binding the target are then used to develop more focused libraries that are then put through the same screening process. This process of screening and preparing new focused libraries typically is repeated several times until a relatively small population of lead compounds is identified. These lead compounds are then subjected to various pharmaceutical analyses to select useful drug candidates.

Although this process is described above for proteins, it will be recognized that there are other molecules and indeed entire biological structures (such as cells or sub-cellular organelles) of biological interest. This discussion of past techniques of drug discovery is directed primarily to proteins for simplicity, as proteins have been the most common targets. It should be recognized, however, that other molecules, structures, and cells have been the target of drug discovery operations and represent alternatives relevant to the present invention.

A primary limitation of many current screening methods is that they require labeling of either the target or ligand and are unable to detect binding complexes directly unless there is some specific (and in many cases rare) interaction that can be detected directly (such as fluorescent quenching of a tyrosine at the binding site of a protein or interaction of a specific optical frequency with only one of the components present in the mixture being analyzed for binding). Further, some methods are unable to determine the strength (affinity) of a target/ligand bond, which is a prime indicator of the specificity of molecular interaction and of the ligand's potential as a drug candidate. The ability to detect the formation and strength of protein/ligand (or, more generally, antiligand/ligand) complexes in a mixture without requiring separation of the components of the mixture from each other would represent a significant advance, and would, for example, further facilitate high-throughput drug-candidate-screening techniques.

Recently, new methods and systems for detecting binding events between ligands and antiligands have been developed in the laboratories of the present inventors utilizing a system that is sensitive to the dielectric properties of molecules and binding complexes, such as nucleic acid hybridization and protein/ligand complexes (see e.g., U.S. Pat. Nos. 6,287,776 and 6,287,874 to Hefti, and PCT/US00/28491 to Chapman et al.). Signals analyzed related to dielectric properties such as the resonant frequency of the system (including the sample as part of the system) and permittivity of the sample. Permittivity is a measure a material's ability to resist the formation of an electric field within it. This material property has conventionally been used to characterize dielectrics used, for example, in the semiconductor fabrication field. However, sensitivity and precision required for measurements in the semiconductor context are of different orders of magnitude than the far higher degree of sensitivity and precision required to detect permittivity differences arising from bonding interactions on the molecular level. The noted patents and application describe how measurements can be taken and used to detect antiligand/ligand binding. In these cases signal analysis primarily comprised detecting a similarity or difference between a test signal and a known signal or comprised measuring a signal change for each of the two potential binding partners added to an otherwise identical buffer and comparing that value to the actual value detected for the combination. In the latter case, if the sum was equal to the measured value, it was understood that no interaction had taken place, while a change was understood to indicate the occurrence of an interaction (and thus a change in the signal).

However, this type of signal analysis did not allow determination of association constants of unknowns without separation of the components. For example, one embodiment described in the PCT application cited above discussed attaching an antibody to the detection region of an apparatus. Attachment in a detection region retains the antibody in that location along with any ligand that becomes bound to the antibody, while flow of solution past the detection region allows unbound ligand to move out of the detection region. The device could be exposed to several different concentrations of the analyte and the response for each concentration measured to provide a dose-response curve, using standard techniques already known in the art that involve separation of bound and unbound species.

In addition to the work that has occurred in the laboratory of the present inventors (exemplified by the publications described above), there has been at least one instance of permittivity measurements at a level of sensitivity sufficient to detect differences in permittivity between a solution of a ligand and a solution of a ligand and an antiligand (Amo et al., Biosensors & Bioelectronics, Vol. 12, No. 9–10, pp. 953–958 (1997)). However, the Amo publication does not teach how to determine binding or how to measure binding affinity since the materials tested were already known to bind. The measurements were merely an indication that a solution containing one component of a known binding pair presented a different permittivity from a solution containing both components. Amo does not attempt to determine and/or quantify ligand/antiligand binding in solution without previously knowing information about the system being investigated (e.g., prior knowledge that binding would occur).

Techniques used to detect molecular binding in solution (and especially to measure binding affinity) in the past have usually required either physical separation of bound and unbound binding pair members from each other, labeling of one or both members of the pair, or, at a minimum, selection of a measurement property that is independent of all but one of the binding pair members. For example, the early techniques that labeled one of the members (e.g., a radioactive or fluorescent label) required separation of bound and unbound materials so that they could be distinguished from each other. This can be seen symbolically by considering component A of a potential A:B binding pair that has been labeled to provide labeled A*. The following equilibrium then occurs upon mixture of the components: $A^* + B \rightleftharpoons A^*:B$. However, when the label * is detected in an un-separated mixture, both $A^*$ and $A^*B$ are detected. The same amount of label is detected regardless of the extent of binding unless $A^*$ is separated from $A^*B$, in which case either can be measured and used to calculate the extent of binding, since the original amount of $A^*$ added to the solution is known.

In special cases, it has been possible to select a measurement property that is independent of all but one of the binding pair members. A known example of this situation occurs when light absorption is used to follow the binding of oxygen to hemoglobin. The spectrum of hemoglobin is different from the spectrum of oxyhemoglobin, and the differences occur at wavelengths that are not measurably absorbed by oxygen or other components of the reaction mixture. Thus, separation of components is not required in order to detect binding. Absorbance increases as oxygen is added to a hemoglobin solution and then levels off as the fraction of hemoglobin converted to oxyhemoglobin approaches 1.

This latter situation can provide graphs that superficially look similar to the graphs obtained by the analysis process of the present invention (which will be described later in detail). See, for example, FIG. 15.5 of the text *Principles of Physical Biochemistry* by van Holde et al., Prentice Hall, New Jersey, 1998, which shows a plot of the change in some measurable parameter X graphed against total ligand concentration. However, closer analysis shows that such graphs are not obtained using data relating to bulk properties of solutions (i.e., properties related to multiple, typically all, of the components in the solution; defined later in detail; q.v.), but to a measurement related to only one component of the solution/mixture being evaluated (rather than all or at least multiple components, as occurs with measurement of bulk properties).

It would be desirable to have an effective general technique for detecting ligand/antiligand binding based on bulk-property measurements, such as permittivity measurements, of unlabeled ligand and antiligand (e.g., small molecule drug candidates and receptor proteins) in solution (1) in the absence of prior knowledge of binding and (2) that does not require detailed prior system information.

SUMMARY OF THE INVENTION

This invention addresses the needs indicated above by providing novel methods for analyzing molecular binding events in which the formation of any ligand/antiligand complexes can be directly detected in a mixture (e.g., a solution) without requiring separation of the components of the mixture from each other. Using this technique, it is possible to screen libraries without the need for labeling of either the target antiligand or ligand. The invention also provides a method for determining the strength of ligand/antiligand binding.

The present invention generally provides methods for detecting binding between ligands and antiligands, utilizing a technique that is capable of elucidating ligand/antiligand binding from electromagnetically detectable bulk property measurements of a mixture of the ligand and antiligand. The invention provides methods for determining the absence or formation and strength of a ligand/antiligand complex based on electromagnetically detectable bulk property measurements of a mixture (e.g., a solution) in which a ligand and an antiligand are mixed.

In one aspect, the invention pertains to a method of detecting ligand/antiligand binding in a mixture. The method involves obtaining electromagnetically detectable bulk property measurements of a mixture of a ligand and an antiligand for each of a plurality of initial ligand concentrations. Some or all of the plurality of the obtained bulk property measurements and corresponding initial ligand concentrations are processed to determine a relationship between the bulk property measurements of the mixture and the initial ligand concentrations as initial ligand concentration changes (increases or decreases). Based on the relationship, the formation or absence of a ligand/antiligand complex is determined. A linear relationship indicates the absence of a ligand/antiligand complex, except in the case in which the contribution to the bulk property by the ligand and the antiligand is identical when they are present separately in the same solution and when they are bound to each other or in the case where the change in bulk property resulting from one of the added potential binding partners dominates the change that results from binding (both of these exceptions can be handled experimentally, as described below). A non-linear relationship indicates the formation of a ligand/antiligand complex. Certain aspects of the methods of the present invention can be implemented using a computer apparatus, and certain aspects of the invention can be embodied in code on computer readable media.

In another aspect, the invention pertains to using a computing apparatus to characterize a ligand/antiligand binding interaction. The method involves providing a mathematical expression describing an electromagnetically detectable bulk property of a mixture of a ligand and antiligand and the relative contributions of the ligand, antiligand and any ligand/antiligand complex in the mixture to the bulk property. The expression is processed to a form that allows a determination regarding ligand/antiligand binding based on a relationship between change in a known parameter of the mixture and a measured parameter of the mixture. The absence or formation of a ligand/antiligand complex in the mixture is determined from correspondence of the processed form of the expression and the relationship. A linear relationship indicates the absence of a ligand/antiligand complex (except in the cases noted above). A non-linear relationship indicates the formation of a ligand/antiligand complex.

BRIEF DESCRIPTION OF THE DRAWINGS

The aspects of the invention described above as well as other features and advantages of the present invention are described below with reference to the drawings:

FIG. 11A shows the absolute permittivity values (e' real part of permittivity) for RNase A accompanying its binding to the either 2'-CMP (triangles), 3'-CMP (diamonds), or 5'-CMP (squares) at various ligand concentrations at 27° C.

FIG. 11 shows the absolute permittivity values (e" imaginary part of permittivity) for RNase A accompanying its binding to the either 2'-CMP (triangles), 3'-CMP (diamonds), or 5'-CMP (squares) at various ligand concentrations at 27° C.

FIG. 11C shows the change in the permittivity (e' real part of permittivity) for RNase A accompanying its binding to the either 2'-CMP (triangles), 3'-CMP (diamonds), or 5'-CMP (squares) at various ligand-to-protein rations at 27° C.

FIG. 11D shows the change in the permittivity (e" imaginary part of permittivity) for RNase A accompanying its binding to the either 2'-CMP (triangles), 3'-CMP (diamonds), or 5'-CMP (squares) at various ligand-to-protein rations at 27° C.

FIG. 11E shows the change in the impedance (Zi, imaginary part of impedance) for RNase A accompanying its binding to the either 2'-CMP (triangles), 3'-CMP (diamonds), or 5'-CMP (squares) at various ligand-to-protein rations at 27° C.

FIG. 11F shows the change in the impedance (Zr, real part of impedance) for RNase A accompanying its binding to the either 2'-CMP (triangles), 3'-CMP (diamonds), or 5'-CMP (squares) at various ligand-to-protein rations at 27° C.

FIG. 11G shows the change in the frequency for RNase A accompanying its binding to the either 2'-CMP (triangles), 3'-CMP (diamonds), or 5'-CMP (squares) at various ligand-to-protein rations at 27° C.

DETAILED DESCRIPTION OF SPECIFIC EMBODIMENTS

Figure 1:
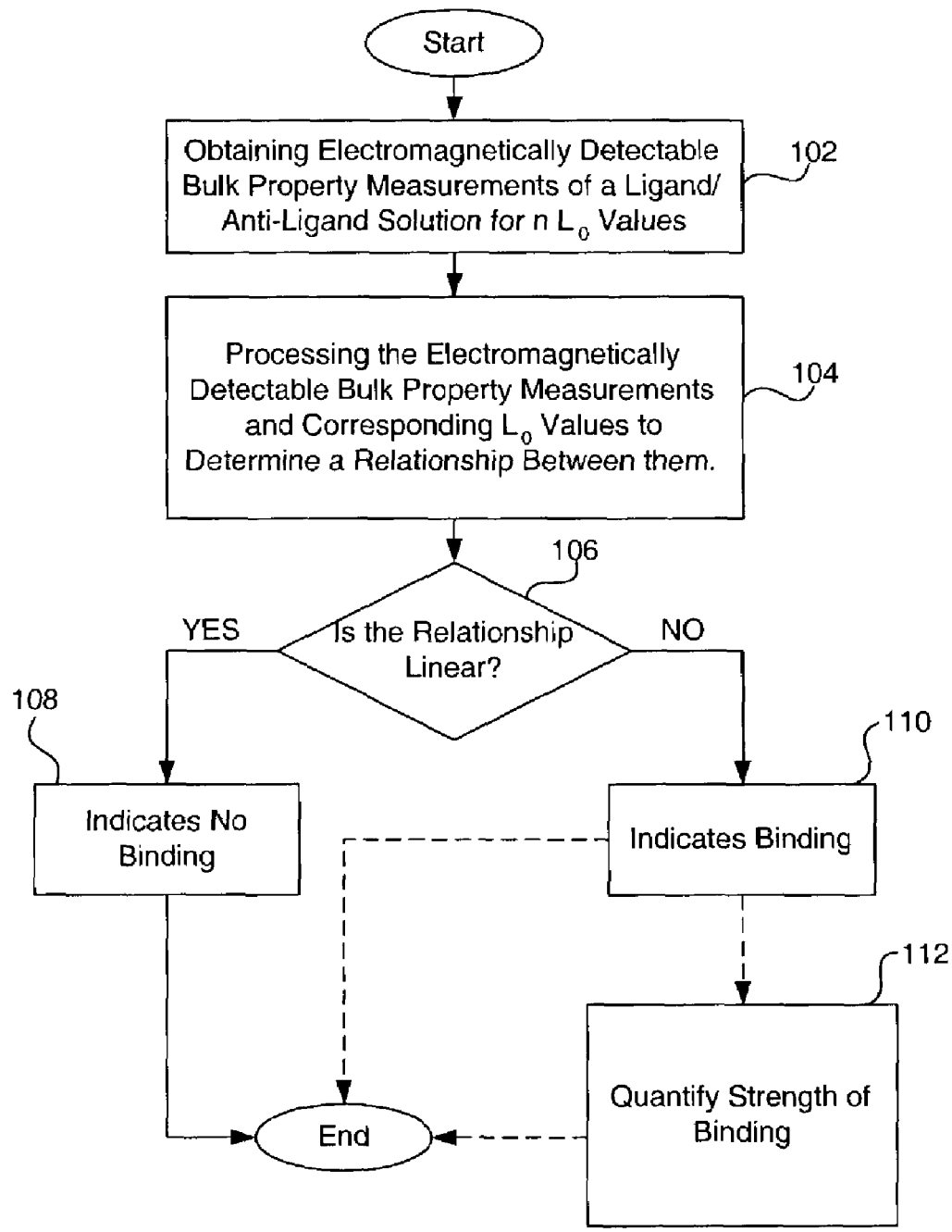
FIG. 1 is a process flow diagram illustrating one embodiment of a method of detecting, and optionally quantifying, ligand/antiligand binding, in accordance with the present invention.

Reference will now be made in detail to specific embodiments of the invention. Examples of the specific embodiments are illustrated in the accompanying drawings. While the invention will be described in conjunction with these specific embodiments, it will be understood that it is not intended to limit the invention to such specific embodiments. On the contrary, it is intended to cover alternatives, modifications, and equivalents within the spirit and scope of the invention as defined by the appended claims. In the following description, numerous specific details are set forth in order to provide a thorough understanding of the present invention. The present invention can be practiced without some or with alternatives to these specific details. In other instances, well known process operations have not been described in detail in order not to unnecessarily obscure the present invention.

When used in combination with "comprising," "a method comprising," "a device comprising" or similar language in this specification and the appended claims, the forms "a," "an," and "the" (e.g., "a method comprising an ABC") include plural reference (i.e., there can be two occurrences of "ABC"). Unless defined otherwise, all technical and scientific terms used herein have the same meaning as commonly understood to one of ordinary skill in the art to which this invention belongs.

I. Definitions

As used herein, "bulk property" means a measurable property of a mixture that is affected by more than one and up to all of the individual components of the mixture being measured (i.e., it is a property to which more than one and up to all of the individual components contribute a measurable signal rather than being determined by only one of the components without significant, measurement-affecting contributions from other components that are present). Accordingly, measurement of individual components of a potential binding interaction, either after separation or by use of a signal that is selective for a particular component, is not a bulk property measurement, as only one component at a time is responsible for the property being measured. For example, measurement of absorbance at a wavelength that is absorbed by only one of the three components—ligand, antiligand, and complex—present in a binary equilibrium mixture, the wavelength being selected so that contributions to the signal of other components in the mixture can be ignored, is not considered to be a bulk property measurement (see the *Principles of Physical Biochemistry* reference cited above for a specific example of a measurement that is not measurement of a bulk property).

The present invention relates to "electromagnetically detectable" bulk properties, that is, bulk properties that can be measured using an electromagnetic signal that interacts with the sample, followed by detection of the signal as modified by the sample. Examples of electromagnetically detectable bulk properties include permittivity, susceptibility, index of refraction, and absorbance. No limits are placed on the frequency (or range of frequencies) being used, as the method works with any frequency electromagnetic signal. However, optical signals (including signals in the infrared and ultraviolet regions) are preferred when used for refraction or absorbance, because of the abundance of existing detection apparatuses that use these frequency ranges, while radio and microwave frequencies are preferred for measurement of permittivity and susceptibility, because of the existence of existing equipment used for these purposes. Frequencies higher than UV are not preferred, as such frequencies have sufficient energy to disrupt some of the bonds present in the organic compounds that are typically used as one or both of the components of a binding complex that is being detected.

As used herein, the term "binding interaction" (sometimes shortened to "binding") refers to the interaction of a molecule of interest (e.g., a "ligand") with another molecule (e.g., an "antiligand"). Examples of ligand/antiligand binding interactions to which the present invention relates are (1) simple, non-covalent binding, such as dipole-dipole interactions, hydrogen bonding, or van der Waals interactions, and (2) temporary covalent bond formation, such as often occurs when an enzyme is reacting with its substrate. More specific examples of binding interactions of interest include, but are not limited to, ligand/receptor, antigen/antibody, enzyme/substrate, DNA/DNA, DNA/RNA, RNA/RNA, nucleic acid mismatches, complementary nucleic acids and nucleic acid/proteins. Binding interactions can occur as primary, secondary, or higher order binding interactions. A primary binding interaction is defined as a first molecule binding (specifically or non-specifically) to a second molecule to form a first molecular interaction complex; a secondary binding interaction is defined as a second molecule binding (specifically or non-specifically) to the first molecular interaction complex; and so on for higher order binding events. The product of ligand/antiligand binding is a ligand/antiligand complex.

The methodology and apparatuses described herein are primarily of interest to detect and predict binding interactions of biological and pharmaceutical importance that occur in physiological situations (such as in a cellular or subcellular membrane or in the cytosol of a cell). Accordingly, preferred binding interactions and properties are those that exist under "physiological conditions," such as would be present in a natural cellular or intercellular environment, or in an artificial environment, such as in an aqueous buffer, designed to mimic a physiological condition. It will be recognized that local physiological conditions vary from place to place within cells and organisms and that artificial conditions designed to mimic such conditions can also vary considerably. For example, a binding interaction may occur between a protein and a ligand in a subcellular compartment in the presence of helper proteins and small molecules that affect binding. Such conditions may differ greatly from the physiological conditions in serum, exemplified by the artificial medium referred to as "normal phosphate buffered saline" or PBS. Preferred conditions of the invention will typically be aqueous solutions at a minimum, although some amounts of organic solvents, such as DMSO, may be present to assist solubility of some components being tested. An "aqueous solution" contains at least 50 wt. % water, preferably at least 80 wt. % water, more preferably at least 90 wt. % water, even more preferably at least 95 wt. % water. Other conditions, such as osmolality, pH, temperature, and pressure, can and will vary considerably in order to mimic local conditions of the intracellular environment in which, for example, a binding event is taking place. The natural conditions in, for example, the cytosol of a cell and a lysosome of that cell, are quite different, and different artificial media would be used to mimic those conditions. Examples of artificial conditions designed to mimic natural ones for the study of various biological events and structures are replete in the literature. Many such artificial media are sold commercially, as exemplified by various scientific supply catalogues, such as the 2000/2001 issue of the Calbiochem General Catalogue, pages 81–82, which lists 60 commercially available buffers with pH values ranging from 3.73 to 9.24 typically used in biological investigations. Also see general references on the preparation of typical media, such as chapter 7 ("The Culture Environment") of *Culture of Animal Cells: A Manual of Basic Techniques*, Third Edition, R. Ian Freshney, Wiley-Liss, New York (1994).

As used herein, the terms "binding partners," "ligand/antiligand," or "ligand/antiligand complex" refers to pairs (or larger groups; see below) of molecules that specifically contact (e.g., bind to) each other to form a bound complex. Such a pair or other grouping typically consists of two or more molecules that are interacting with each other, usually by the formation of non-covalent bonds (such as dipole-dipole interactions, hydrogen bonding, or van der Waals interactions). The time of interaction (sometimes referred to as the on-off time) can vary considerably, even for molecules that have similar binding affinities, as is well known in the art. Examples include antibody-antigen, lectin-carbohydrate, nucleic acid-nucleic acid, and biotin-avidin pairs. Other examples will be readily apparent to those skilled in the art. The word "ligand" is commonly used herein to refer to any molecule for which there exists another molecule (i.e., an "antiligand") that binds to the ligand, owing to a favorable (i.e., negative) change in free energy upon contact between the ligand and antiligand. There is no limit on the size of the interacting substances, so that a ligand (or an antiligand) in this broad sense can consist of either an individual molecule or a larger, organized group of molecules, such as would be presented by a cell, cell membrane, organelle, or synthetic analogue thereof. As used herein, "ligand" and "antiligand" both have this broad sense and can be used interchangeably. However, it is recognized that there is a general tendency in the field of biology to use the word "ligand" to refer to the smaller of the two binding partners that interact with each other, and this convention is followed whenever possible.

As used herein, the term "ligand/antiligand complex" refers to the ligand bound to the antiligand. The binding can be specific or non-specific, and the interacting ligand/antiligand complex are typically bonded to each other through non-covalent forces such as hydrogen bonds, Van der Waals interactions, or other types of molecular interactions.

As used herein, the term "sample," "sample mixture," or "sample solution" refers to the materials being investigated (e.g., the ligand, antiligand and ligand/antiligand complex, if any) and the medium/buffer in which the materials are found. Examples of preferred media are physiologically acceptable buffer solutions, such as described herein.

As used herein, the term "fluid reservoir" refers to any location, without regard to physical size or shape, where fluid is being maintained in a position that is coupled to a signal path, so that a signal resulting from interaction of a test signal with a sample in the detection region of the "fluid reservoir" can be detected. "Fluid reservoir" refers more to the fluid itself than to the container in which the fluid is located. In its simplest form, therefore, "fluid reservoir" can refer to a fluid droplet or layer formed on a flat surface and maintained at that location by inertia and/or surface tension. Such arrangements are sometimes used in various "chip" designs commonly used in genomics in which a sample fluid is washed across the surface of a chip that has specific molecular probes (usually DNA fragments of know sequence) attached at known locations on the surface. The "fluid reservoir," however, can be and often is contained within physical walls that restrain movement of the fluid, such as vertical walls that constrain gravitational spreading (as in the side walls of test tube or microtitre plate), completely surrounding walls (as in a sealed container), or partially surrounding walls that direct and/or permit motion in a limited number of directions (such as the walls of a tube or other channel). The last of these named possibilities is often referred to herein as a "fluid channel" and occurs commonly in situations were a fluid is being moved from one location to another (such as in a microfluidics chip) to allow interaction with other samples and/or solutions containing reagents or to allow multiple samples to be transported past a single detection region.

As used herein, the term "signal path" refers to a transmission medium that supports the propagation of the desired electromagnetic test signal. In one embodiment the signal path comprises a coplanar waveguide or coaxial cable along with a probe and that part of the sample that interacts with the signal (i.e., the "detection region;" see below). Other signal paths are also possible depending on the particular bioassay system used to obtain the bulk property measurements.

As used herein, the term "detection region" refers to the region (all or a portion) of a fluid reservoir (e.g., a fluid transport channel in a microfluidics chip or a well of a multiwell plate) that receives and interacts with the electromagnetic signal radiated from the signal path in a manner that is detected by the apparatus being used. Thus, while some signal may interact with sample at another location (e.g., an adjacent well of a microtitre plate impinged by stray electromagnetic radiation from a probe head), such extraneous interactions, if not detected by the apparatus being used, would not cause the adjacent region to be part of the "detection region." On the other hand, if a signal were to interact with a portion of a bulk sample, all of the volume of the bulk sample that interacts with the signal so as to produce a modified signal that could be detected by the apparatus would be considered to be part of the "detection region." Detection regions of an apparatus used for a preferred implementation of the present invention are typically relatively small. This is particularly true when the purpose is testing for potential candidate drugs from a library of test compounds for ability to interact with a target receptor, as the amount of each individual compound available for a specific assay is often low. Accordingly, detection region volumes of less than 1 ml ($1 \times 10^{-6}$ m$^3$) are preferred. Even smaller detection regions are more preferred, such as 1 $\mu$l ($1 \times 10^{-9}$ m$^3$), 1 nl ($1 \times 10^{-12}$ m$^3$), or 1 pl ($1 \times 10^{-15}$ m$^3$), and ranges between all of these individually named volumes. Smaller volumes 1 pl can be used but are not preferred, as smaller volumes are unlikely to contain a statistically significant number of molecules of interest under the conditions of temperature, pressure, and concentration normally used with physiological samples.

As used herein, the term "initial ligand concentration" refers to the total mass of a solute added to a solvent or solution related to the total volume or mass of the solution formed thereby (typically express by molarity or any of the common other means of expressing concentration, such as molality or percent weight or volume; mathematical operations will differ slightly from those described here, which are for molarity, if concentration is expressed in other units). Thus, as used herein, the initial concentration of a ligand depends only upon the amount of ligand added and is independent of whether or not the ligand binds with an antiligand present in the solution. This might equally be called total ligand concentration, since both the free ligand and the ligand present in any complex that is formed are included.

II. Introduction

A. General

The present invention generally provides methods for analyzing binding interactions involving the binding of an antiligand (for example, a cell or a protein, such as a receptor, an enzyme, or an antibody) to various types of ligands (such as inhibitors, agonists, antagonists, substrates, drug candidates, and the like). More specifically, the invention provides methods for label-free detection of ligand/antiligand binding in a mixture (typically a solution) without requiring separation of the components of the mixture from each other. Certain methods include screening large libraries of molecules to identify those that bind to a particular biological macromolecule of interest (e.g., a receptor or other protein having a binding site that provides control of a biological activity). Such methods have particular utility in drug discovery programs. Other methods include the use of known proteins to assay for the presence of a particular ligand in a sample (and vice versa). Still other methods involve the use of data-processing techniques to quantify the strength of an established or newly discovered ligand/antiligand bond. Certain aspects of the methods of the present invention can be embodied in code on computer readable media.

B. Bio-Assay Systems

The methods of the present invention are conducted with electromagnetically detectable bulk property measurements of a mixture containing a ligand and antiligand. In general, the bulk property measurements are obtained using a bioassay system. A typical system includes a signal source and a signal detector (which can be the same or different components of the system) electromagnetically coupled with a detection region of a fluid reservoir that contains a sample solution that contains, or that is suspected of containing, a ligand and an antiligand. A electromagnetic test signal is launched from the signal source, and a transmitted and/or reflected signal, as modulated by the presence of the ligand, antiligand, and ligand/antiligand binding complex (if any) in the solution, is detected and then used to determine the formation of any binding complex. As an optional step, if a complex is present, the strength of the binding can be determined (usually expressed as an association constant, $K_A$, or a dissociation constant, $K_D$).

The present invention makes use of the observation that useful information concerning the binding interactions of a ligand and antiligand in a mixture (e.g., solution), including the absence or formation of a ligand/antiligand complex, can be obtained through measurement and analysis of an electromagnetically detectable bulk property of the mixture. Examples of electromagnetically detectable bulk properties in accordance with the present invention are noted above. These bulk properties can be observed by applying an electromagnetic signal launched from a signal source, and collecting a transmitted and/or reflected signal, as modulated by the presence of the ligand, antiligand and ligand/antiligand binding complex (if any) in the mixture. This signal represents an electromagnetically detectable bulk property measurement of the mixture and is used to determine the absence or formation of any binding complex and, if a complex is formed, optionally to determine the strength of the binding.

A variety of bioassay systems can be used to obtain electromagnetically detectable bulk property measurements suitable for implementing the present invention. Among these are systems including instruments designed to obtain measurements of dielectric properties (e.g. permittivity) of solution containing ligands and antiligands of interest. Suitable systems include Multipole Coupling Spectroscopy (MCS) systems developed in the laboratories of the present inventors and further described a number of issued patents and pending patent applications (a list of these patent documents is included at the end of this specification). One such system, when used in accordance with the present invention, is generally composed and configured as follows: (1) a co-axial resonating detector operating in the microwave range (e.g., at 1.3 GHz), (2) a 8719ET network analyzer from Agilent Technologies, (Santa Rosa, Calif.), (3) an automated fluidic module (AFM) for drawing samples into a flow cell, the AMF comprising a Cavro XP 3000 digital pump and a Cavro smart valve (6 port) from Tecan (Santa Clara, Calif.), (4a) a thermal enclosure based on a zero gradient oven design which houses both the detector and a sample flow cell, (4b) a high resolution thermal controller (PID) and (5) a PC computer running Lab-VIEW™ software from National Instruments Corporation (Austin, Tex.) to communicate between all these components. The flow cell (a polyimide tube with an 0.0285" I.D. and an 0.0305" O.D. from HV Technologies, Trenton, Ga.) is mounted on the top of the coaxial resonating detector such that only the wall of the tubing separates the detector and the fluidic sample. The AFM is used to draw the fluidic samples into the detector region of the tube for measurement.

As noted above, the present invention can be used with any electromagnetically detectable bulk property measurements, and permittivity is just on example of such a bulk property. Comparable bioassay systems incorporating detection instruments for bulk properties such as susceptibility, index of refraction, and absorbance, such as are known to those of skill in the art, can also be used. An example of a measurement of index of refraction, including a description of the apparatus and bioassay system used, is set out in the following examples.

III. Binding Detection and Quantification

A. Detection of Binding

The ability to use a bulk property measurement to detect whether or not ligand/antiligand binding takes place in a mixture, and the strength of any such binding, depends upon the ability to relate a bulk property measurement of the mixture to the formation of a ligand/antiligand complex in the mixture. This is complicated by the fact that the presence of all components of the mixture must be taken into account. This includes the unbound antiligand and ligand as well as the ligand/antiligand binding complex, if any.

It has been discovered that information sufficient to establish whether or not ligand/antiligand binding has occurred in a solution can be elucidated from electromagnetically detectable bulk property measurements of a mixture (e.g., solution), without requiring separation of the components of the mixture from each other and without having made a similar measurement in the past to which a signal comparison can be made, by establishing a relationship between the bulk property measurements of the mixture and the initial ligand concentrations as initial ligand concentration is varied. The formation or absence of a ligand/antiligand complex can be determined based on the nature of this relationship. The signals and resulting plots that are obtained are different from the signal obtained when components are separated prior to measurement or otherwise measured separately (e.g., the typical plots of binding fraction vs. concentration used to obtain equilibrium constants, which require measurement of, e.g., the bound fraction of a labeled ligand, separated from unbound labeled ligand).

One embodiment of a method in accordance with the present invention is illustrated in the process flow of FIG. 1. At 102, electromagnetically detectable bulk property measurements of a solution of a ligand and an antiligand for each of a plurality (n) of initial ligand concentrations ($L_0$) are obtained. The bulk property measurements can be, for example, permittivity measurements acquired using, for example, a bioassay system such as the MCS system described above. At 104, a plurality of the obtained electromagnetically detectable bulk property measurements and corresponding initial ligand concentrations are processed to determine a relationship between the bulk property measurements of the solution and the initial ligand concentrations as initial ligand concentration changes (e.g., increases).

The present inventors have established that the formation or absence of a ligand/antiligand complex can be determined based on whether the relationship between electromagnetically detectable bulk property measurements of the solution and the initial ligand concentrations as initial ligand concentration is varied (e.g., increased) is linear or non-linear. At 106, this determination is made. For example, the electromagnetically detectable bulk property data values can be plotted against the initial ligand concentration values or, preferably, existence of linear or non-linear relationships can be determined mathematically. A linear relationship indicates that there is no (at least to the extent measurable by the detection system being used) binding of the ligand and antiligand to form a ligand/antiligand complex (108) or that the complex formation is not detectable for some reason (such as the special cases previously mentioned). A non-linear relationship indicates that there is binding of the ligand and antiligand to form a ligand/antiligand complex (110).

As noted previously, it should be understood that it is possible (1) that the electromagnetically detectable bulk property of a solution containing a ligand and an antiligand can be identical when they are simply mixed without binding and when they are bound to each other or (2) that changes resulting from the addition of one component can overwhelm the small signal that results from a binding interaction. In such cases, the method and product of the present invention can be ineffective to determine binding without modification of the experimental technique. However, at least two general techniques are available for determining whether or not a linear relationship is caused by the absence of binding or by one of these special circumstances. One such technique is simply to change the buffer in which binding is being measured. Since the buffer contributes to the bulk property and also influences the contributions to the overall bulk property by the individual components, making a measurement in a different buffer will change an apparently linear relationship to a non-linear one if binding is in fact taking place. On the other hand, if there is no binding, changing the buffer will not change a linear relationship to a non-linear one. This effect is understood to be caused by solvation, ionization, or other effects of the buffer on the ligand, antiligand, and complex, as those effects are likely to differ for different buffer solutions, so that accidental cancellation effects in one buffer are not likely to exist in another. Here "different buffer" refers to buffers that differ by pH but contain the same constituents in different ratios, as well as buffers that contain different constituents.

A second technique is used in cases where the contribution of one component of the ligand/antiligand complex overwhelms the contribution of the complex. The component that makes the overwhelming contribution is referred to as the "over-effective component." In such situations a compensator can be added in such a manner that it reduces the effects of added over-effective component. As an example, consider the bulk property of permittivity and what would be needed to cancel out the effects of an over-effective component that has a positive effect on the bulk permittivity of the test sample to which it is being added. Addition of a compensator that has a negative effect on permittivity, in an amount that cancels the effect of the over-effective component, allows detection of the relatively small change due to binding relative to an unchanging or only slightly changing background rather than a background permittivity that changes rapidly as a result of addition of the over-effective component alone. This allows detection of a small signal against a stable background rather than attempting to detect a small signal in the presence of a rapidly changing signal. Techniques also exist for using a compensator that has the same effect as the over-effective component, and decreasing the compensator while the component is increasing. This effectively results in no overall change in the bulk property being measured unless binding takes place.

In actual practice, this latter technique is most readily handled by titrating the "over-effective component" in the buffer of interest to determine the change in bulk property as the concentrations changes for that component (e.g., change in permittivity per change in concentration unit). The compensator is then titrated in the same buffer to determine its, e.g., change in permittivity per change in concentration unit. When two solutions are prepared for the binding determination, e.g., solution A—protein antiligand in buffer—and solution B—both protein antiligand and ligand in buffer (here assuming that the ligand is the over-effective component)—the compensator is added to solution A to a concentration appropriate for compensating the maximal amount of ligand present in solution B. When one is adding a liquid compensator (as in the case of DMSO, which has been used experimentally for this purpose), this addition dilutes the constituents of solution A. This dilution can be accounted for by adding water to solution B to the same extent as compensator in solution A.

The measurement is then handled in the normal manner. Solution B is titrated into solution A, achieving the usual variation in ligand concentration that generates a binding curve. However, because of the additional steps above, while one is increasing the concentration of ligand in the various mixtures, one is simultaneously decreasing the concentration of the compensator. Since the concentration of compensator is chosen to balance the ligand permittivity change, this results in no change in permittivity of the bulk solution due to the titration itself (or at least in minimizing the change, if the compensation is imperfect; perfect compensation is not required, although it is preferred). If the compensation is precise, the only remaining change present should represent a binding event. After the saturation point of the binding event, i.e., after the "kink" in the curve, there is no further change in permittivity, as the over-effective component and the compensator counteract each other. The resulting binding curve should therefore be flat after the saturation point.

It will be recognized that alternative techniques of handling a compensator exist, such as by adding different specific amount of a compensator to a solution as the concentration of the component being compensated for changes. All such methods are designed so that the bulk property being measured remains as constant as possible for the total mixture while there is a change in concentration of the over-effective component. In this manner, the signal from complex formation is not overwhelmed and is more easily detected.

This requirement for additional testing, however, does not detract from the general effectiveness of the present invention for the determination of ligand/antiligand binding in the vast majority of cases, even without use of the compensation or buffer change techniques outlined above. Moreover, the electromagnetically detectable bulk property measurements obtained in accordance with the present invention are necessarily limited by the prevailing state of the art in electromagnetically detectable bulk property measurement devices and techniques. It is to be expected that future improvements in electromagnetic detection of bulk properties will result in enhanced sensitivity that, for example, will be capable of detecting differences in bulk properties that are not presently detectable. In such cases, some of the additional techniques (changing of buffers or use of compensators, for example) will no longer be required as noise relative to signal decreases and it becomes easier to distinguish linear from non-linear relationships.

Figure 2A:
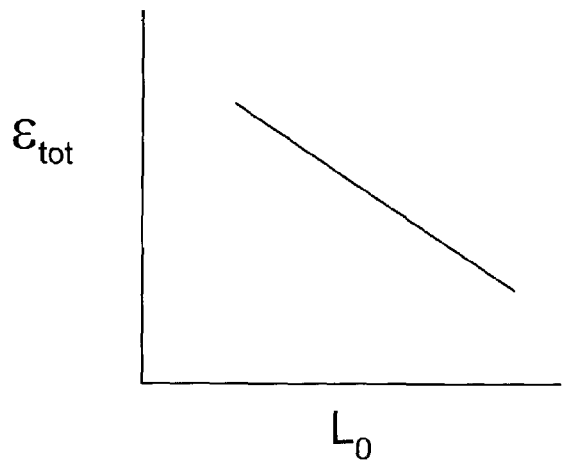
FIGS. 2A–C illustrate hypothetical plots of a bulk property measurement vs. initial ligand concentration for solutions in which ligand/antiligand binding does (2B, 2C) and does not (2A) occur, in accordance with the present invention.
Figure 2B:
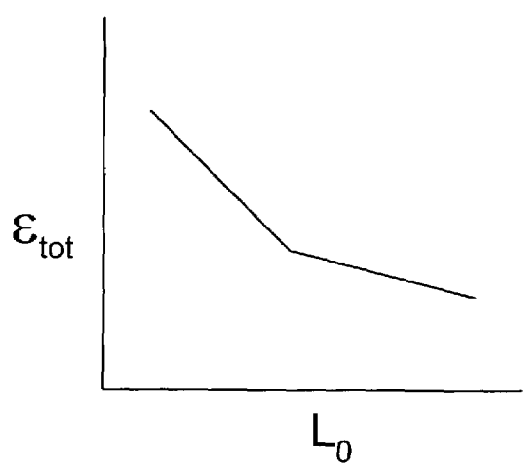
Figure 2C:
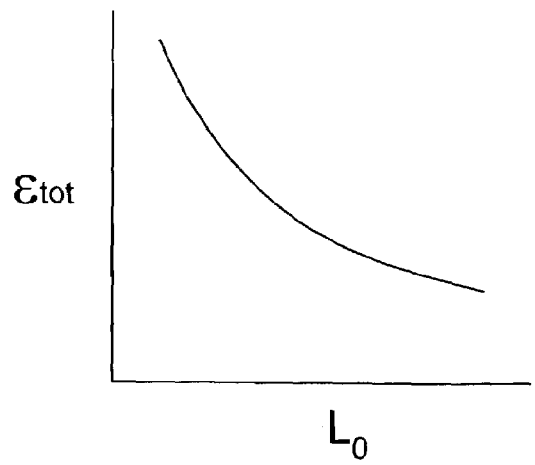

FIG. 2A illustrates a representative example of a plot of an electromagnetically detectable bulk property ($\epsilon$) vs. initial ligand concentration ($L_0$) data for a solution of a ligand and an antiligand for which no binding occurs. The plot indicating no binding is linear. FIGS. 2B and 2C illustrate representative examples of plots of the bulk property ($\epsilon$) vs. initial ligand concentration ($L_0$) data for solutions of a ligand and an antiligand for which binding does occur. The plots indicating binding are non-linear. It should be noted that the data can be plotted using a variety of formats to illustrate a variety of aspects of the data. Plots of the data in this format illustrate particularly well the linear and non-linear relationships.

While not wishing to be bound by theory, it is believed that a mathematical basis for the observed relationships has been established. As noted above, while it would be desirable to be able to detect the formation of a ligand/antiligand complex by a direct measurement of that component of the solution, the bulk property measurements of the solution are the total bulk property (here exemplified by permittivity, $\epsilon_{tot}$), including contributions from any unbound ligand and antiligand. Using a representative case in which a ligand and antiligand bind with a 1:1 stoichiometry, the relative contributions of the components of the solution to the total bulk property ($\epsilon_{tot}$) can be isolated. From this relatively simple case, generalizations can be made to more complex stoichiometries. It has been observed that the addition of small amounts (e.g., millimolar and lower (to micro- and nanomolar) concentrations) of a ligand, antiligand, and/or ligand/antiligand complex to an inert buffer often causes only a small linear change of a particular electromagnetically detectable bulk property of the resulting solution. Accordingly, an electromagnetically detectable bulk property of a solution containing ligand (L), antiligand (A) and ligand/antiligand complex (C) may be expressed as follows:

$$\epsilon_{tot} = \epsilon_B + \epsilon_A A + \epsilon_L L + \epsilon_C C \qquad \text{(Formula 1)}$$

where $\epsilon_{tot}$ and $\epsilon_B$ are the bulk property of the solution and the buffer ("buffer" should be understood to include everything in the mixture (solution) other than L, A and C), and $\epsilon_A$, $\epsilon_L$, $\epsilon_C$ and L, A, C are the molar bulk property and molar concentrations of ligand, antiligand and complex, respectively. (In this example calculation, the bulk property is exemplified by permittivity, represented by the standard permittivity symbol $\epsilon$. However, it should be recognized that E is an exemplary bulk property, and the mathematical operations discussed here are independent of the physical nature of the bulk property.)

A molar bulk property, such as molar permittivity, is a characterization of a component of a mixture (e.g., a solute in a solution). As the concentration of the solute changes, the bulk property (e.g., permittivity) of the whole solution changes. Since in cases of low concentration the change in bulk permittivity is a linear function of concentration, we can define molar permittivity of a solute in a solution as a ratio of the change in bulk permittivity of the solution over the change in molar concentration of the solute.

If $A_\infty$, $L_\infty$ and $C_\infty$ are the final concentrations that result when $A_0$ and $L_0$ are combined in solution, $A_0$, $L_0$, $A_\infty$, $L_\infty$ and $C_\infty$ are related as follows:

$$\frac{1}{K_D} = \frac{C_\infty}{A_\infty \cdot L_\infty} = \frac{C_\infty}{(A_0 - C_\infty)(L_0 - C_\infty)}$$

where $K_D$ is an equilibrium constant (dissociation constant) indicating binding affinity of A and L.

This equation can be solved for $C_\infty$ by applying the quadratic equation as follows:

$$(A_0 - C_\infty)(L_0 - C_\infty) = K_D C_\infty$$

$$A_0 L_0 - (A_0 + L_0) C_\infty + C_\infty^2 = K_D C_\infty$$

$$A_0 L_0 - (A_0 + L_0 K_D) C_\infty + C_\infty^2 = 0$$

$$C_\infty = \frac{A_0 + L_0 + K_D - ((A_0 + L_0 + K_D)^2 - 4 A_0 L_0)^{\frac{1}{2}}}{2}$$

Thus, the final concentration of the complex, $C_\infty$, can be expressed as a function, g, of the initial concentrations of the ligand and antiligand and the equilibrium binding constant: $g(L_0, A_0, K_D)$. Substituting the relationships determined above into the original expression of the electromagnetically detectable bulk property of the solution, $\epsilon_{tot} = \epsilon_B + \epsilon_A A + \epsilon_L L + \epsilon_C C$, yields:

$$\begin{aligned}\epsilon_{tot} &= \epsilon_B + \epsilon_A A_\infty + \epsilon_L L_\infty + \epsilon_C C_\infty \epsilon_A \\ &= \epsilon_B + \epsilon_A (A_0 - C_\infty) + \epsilon_L (L_0 - C_\infty) + \epsilon_C C_\infty \\ &= \epsilon_B + \epsilon_A A_0 + \epsilon_L L_0 + (\epsilon_C - \epsilon_A - \epsilon_L) C_\infty\end{aligned}$$

This relationship may be simplified (the buffer bulk property, $\epsilon_B$, is a constant, and the antiligand concentration is usually fixed, so $\epsilon_B + \epsilon_A A_\infty$ is a constant) to yield:

$$\begin{aligned}\epsilon_{tot} &= \alpha + \beta L_0 + \gamma C_\infty \\ &= \alpha + \beta L_0 + \gamma g(A_0, L_0, K_D)\end{aligned}$$

From this relationship, $\epsilon_{tot} = \alpha + \beta L_0 + \gamma_g(L_0, A_0, K_D)$, the following can be determined. If there is no binding, there is no complex, and g=0. In this case, the formula simplifies to the equation for a straight line (y=mx+b), explaining the linear relationship observed when there in no ligand/antiligand binding, illustrated in FIG. 2A. If there is binding, there is binding complex at a concentration other than zero, and g is a non-zero value. In this case, the formula is not that of a straight line and corresponds to a non-linear relationship and plot, such as are illustrated in FIGS. 2B and 2C (of course the non-linear plot may have a variety of other shapes, depending of the value of g). From another perspective, if the calculated value of γ is different than zero to a statistically significant extent, there is binding.

As noted above, the foregoing assumes a ligand and antiligand binding with a 1:1 stoichiometry having a binding interaction characteristic of the following simple equilibrium relationship:

where A represents the antiligand, L represents the ligand, and C represents the antiligand/ligand complex.

However, if a ligand interacts with an antiligand more than once, a different relationship governs. In the case of a ligand interacting with an antiligand twice, first the ligand binds to the antiligand forming complex $C_1$. Then the ligand interacts with this complex to form complex $C_2$. This 2:1 stoichiometry may be described by the following equilibrium relationship:

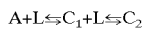

In this case there are two reactions. Each reaction has its own equilibrium constant. If a bulk property of the antiligand/ligand mixture is measured as more and more ligand is added, and these measurements are plotted, a curve as illustrated in FIG. 3 results.

Figure 3:
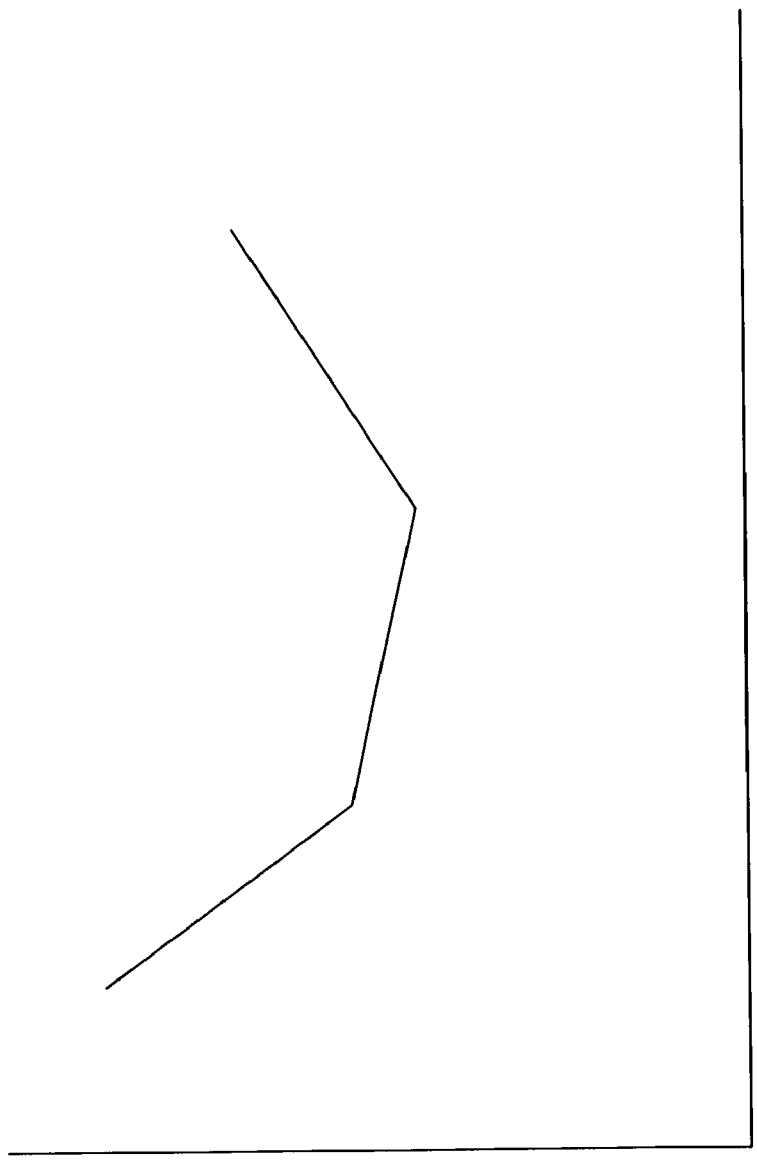
FIG. 3 illustrates a hypothetical plot of a bulk property measurement vs. initial ligand concentration for solutions in which ligand/antiligand binding occurs according to 2:1 stoichiometry, in accordance with the present invention.

The curve depicted in FIG. 3 has 3 segments. The linear left segment of the curve represents the change in an electromagnetically detectable bulk property, $\epsilon'$, of the solution as ligand is added up to the initial ligand concentration at which formation of the first complex $C_1$ begins. The linear middle segment represents the change in the measurable bulk property after formation of complex $C_1$ is complete, up to the initial ligand concentration at which formation of the second complex $C_2$ begins. The linear right segment represents the change in the electromagnetically detectable bulk property of the solution as ligand is added after formation of complex $C_2$ is complete. The regions of curvature represent the concentrations at which binding to form the complexes is occurring but not yet complete (the left curving region indicating formation of $C_1$ and the right curving region indicating formation of $C_2$).

The slopes of the various sections of the curve can vary depending on the relative bulk property measurements of the antiligand, ligand and the complexes as well as the sizes of the two equilibrium constants and the particular buffer being used. Similarly, if a ligand and antiligand bind according to a stoichiometry greater then 2:1, a curve with additional segments results. If the ratio is 1:2 (ligand:antiligand) or another ratio with excess binding of antiligand, similar considerations hold. Thus, the basic concept that antiligand/ligand binding interactions can be detected by observing the linearity or non-linearity of the relationship between changing initial ligand concentration and an electromagnetically detectable bulk property of the solution holds for any stoichiometry, provided that a statistically significant measurement can be obtained.

As noted above, in one implementation, the present invention relates to methods for screening ligands for those having binding affinity for an antiligand protein target of interest. In this implementation, the method described above for determining binding is conducted for a plurality of ligands. The ligands can include species selected from group consisting of peptides, oligosaccharides, nucleic acids, lipids, antibodies or fragments thereof, cells, steroids, and a small molecule drug candidate library of compounds, among others. Similarly, the method described below with respect to quantifying the binding strength of ligand/antiligand complexes can also be applied in this screening implementation. As such, the present invention is useful within the fields of fundamental biomedical and biochemical research, especially drug discovery and medical diagnostics.

B. Quantification of Binding Strength

The existence of non-linearity in a plot representing the relationship between an electromagnetically detectable bulk property of a mixture (e.g., solution) and the initial ligand concentration is sufficient to indicate binding. However, the character of the non-linearity, as defined by the mathematical relationships described above, can also yield important information regarding the nature (e.g., the strength) of the bond with further processing. Further processing of the data can establish an equilibrium binding constant $K_{EQ}$ (alternatively expressed as either an association constant, $K_A$, or a dissociation constant, $K_D$, where $K_D=1/K_A$) for the ligand, antiligand and complex in a solution to provide a quantification of the strength of the ligand/antiligand bond (FIG. 1, 112, optional). Alternatively, binding strength can be expressed in other manners than as an equilibrium constant (e.g., free energy of binding or percent bound ligand at a particular concentration) by modifying the calculations shown herein in manners known for expressing such other units.

Figure 4:
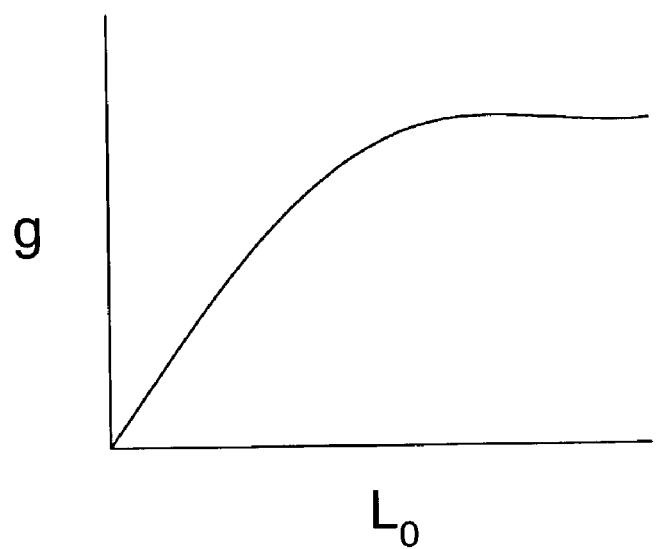
FIG. 4 illustrates a hypothetical plot of a function representing the contribution of a ligand/antiligand complex to an electromagnetically detectable bulk property of a solution vs. initial ligand concentration, in accordance with the present invention.

Given that there is an equilibrium between the bound and unbound components of a solution in which ligand/antiligand binding occurs (A+L⇌C), a plot of the function g representing the final concentration of the complex, $C_\infty$, vs. initial added ligand concentration, $L_0$, will rise and then flatten with increasing initial ligand concentration, as illustrated in FIG. 4. Building on the theory described above, a further theory is advanced to explain the physical data findings for various ligand/antiligand combinations.

As described above, where no measurable ligand/antiligand binding occurs in a solution, a plot of an electromagnetically detectable bulk property of the solution vs. the initial ligand concentration is linear. This is analogous to the situation where, in a solution of a ligand and antiligand that do bind, the initial concentration of ligand is insufficient for measurable binding to take place. Once a sufficient concentration of the ligand is introduced into the solution for ligand/antiligand binding to begin, it will occur according to the function g, described above.

Figure 5A:
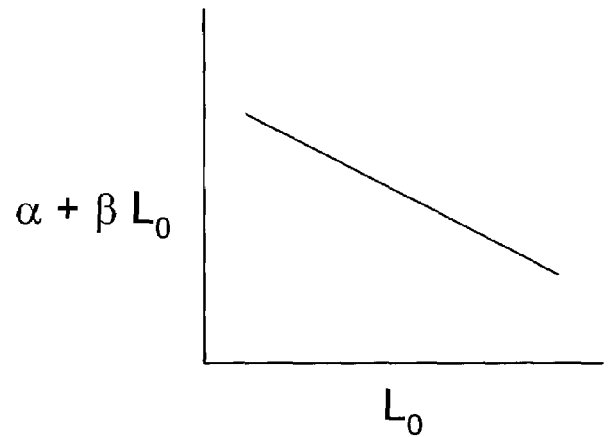
FIGS. 5A–C illustrate hypothetical plots representing contributions to an electromagnetically detectable bulk property of a solution of a ligand and an antiligand with relatively high binding affinity, in accordance with the present invention.
Figure 5B:
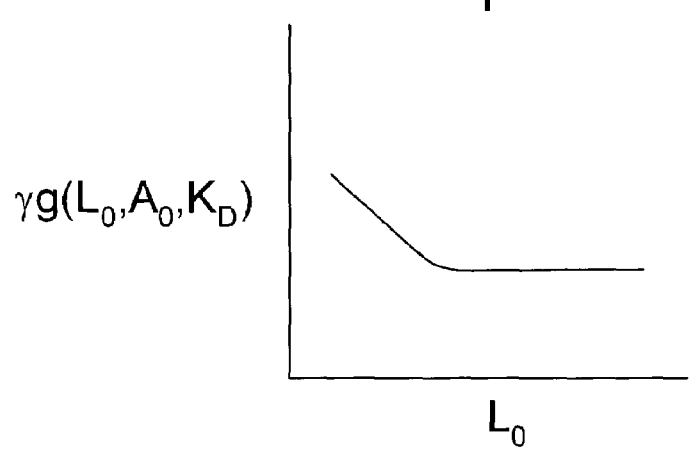

Thus, the plots of total bulk property of a solution of FIGS. 2B and 2C may be broken down into contributions that occur before there is sufficient concentration of the ligand introduced into the solution for ligand/antiligand binding to begin, and into contributions that occur after binding begins. Before, the contribution is governed by the equation for a straight line, in this case expressed as $\epsilon=\alpha+\beta L_0$. After, the contribution is governed by the function $\gamma g(A_0,L_0,K_D)$. This is illustrated in FIGS. 5A, B and C and 6A, B and C. The difference in the shape of the plotted curves, and in particular, the sharpness with which the curve changes, is attributable to differences in the equilibrium binding constant, $K_A=1/K_D$, for the particular ligand/antiligand interaction. The value of $K_A$ is proportional to the binding strength of a particular ligand/antiligand complex ($K_D$ is inversely proportional to the strength of binding).

Figure 5C:
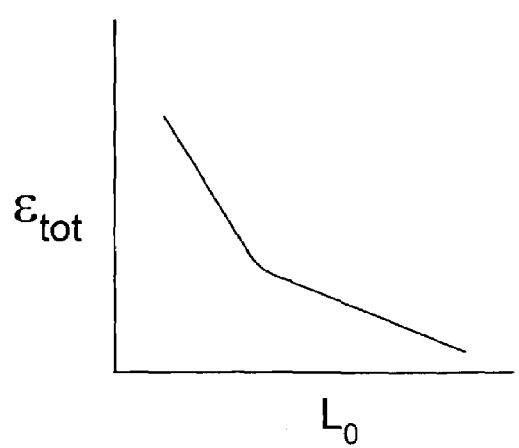
Figure 6A:
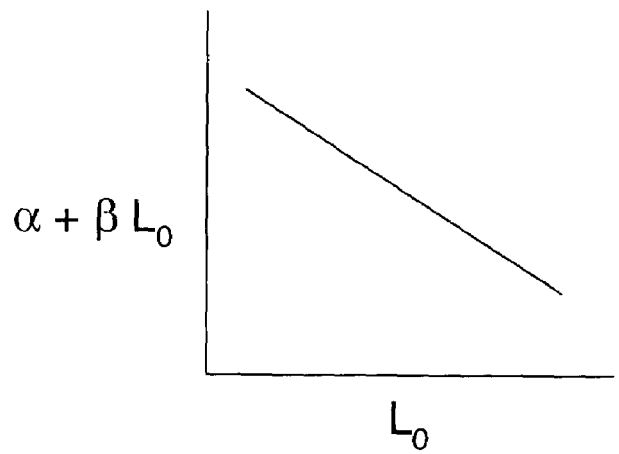
FIGS. 6A–C illustrate hypothetical plots representing contributions to an electromagnetically detectable bulk property of a solution of a ligand and an antiligand with relatively low binding affinity, in accordance with the present invention.
Figure 6B:
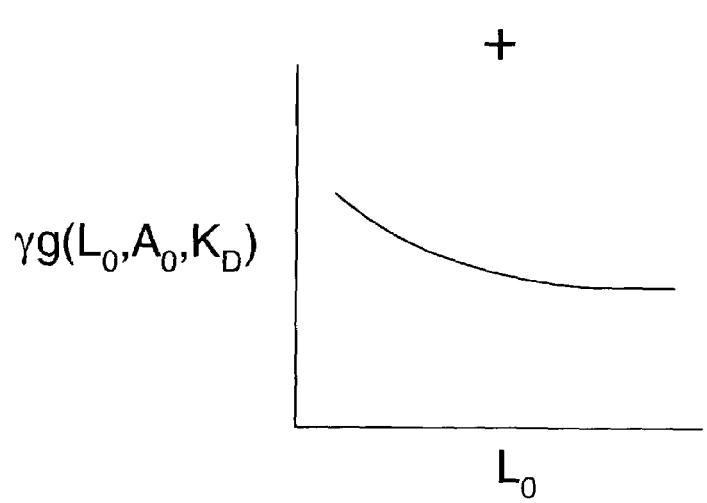
Figure 6C:
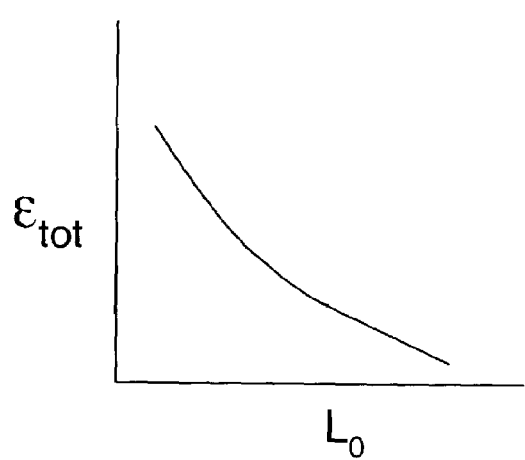

Therefore, in accordance with the present invention, an indication of the strength of the bond between a particular ligand and antiligand can be obtained from the shape of the solution bulk property vs. initial ligand concentration plot. A sharp curve, such as illustrated in FIG. 5C, indicates a relatively high $K_A$ (low $K_D$) and thus a strong bond. A gentle curve, such as illustrated in FIG. 6C, indicates a relatively low $K_A$ (high $K_D$) and thus a weak bond.

While it is not possible to determine the equilibrium binding constant by solving the equation described above for $K_A$, further mathematical techniques can be applied in order to solve for $K_A$, as in the following example.

Given the equation $\epsilon_{tot}=\alpha+\beta L_0+\gamma g(A_0,L_0,K_D)$, it can be seen that $\epsilon_{tot}$ is a function of $L_0$ and $K_D$ ($F(L_0,K_D)$). $\epsilon_{tot}$ is a measured value and $L_0$ is known. If $K_D$ is fixed, $\epsilon_{tot}$ can be predicted from $L_0$. Then, $K_D$ can be adjusted until the predicted and measured values of $\epsilon_{tot}$ are as close as possible according to a nonlinear least squares analysis defined as follows:

$$\{(^iL_0,{}^i\epsilon_{tot})|i=1, 2, \ldots n\} \text{ measurements}$$

find $K_D$ such that $$\Sigma[{}^i\epsilon_{tot}-F({}^iL_0,K_D)]^2 \text{ is a minimum.}$$

Figure 7:
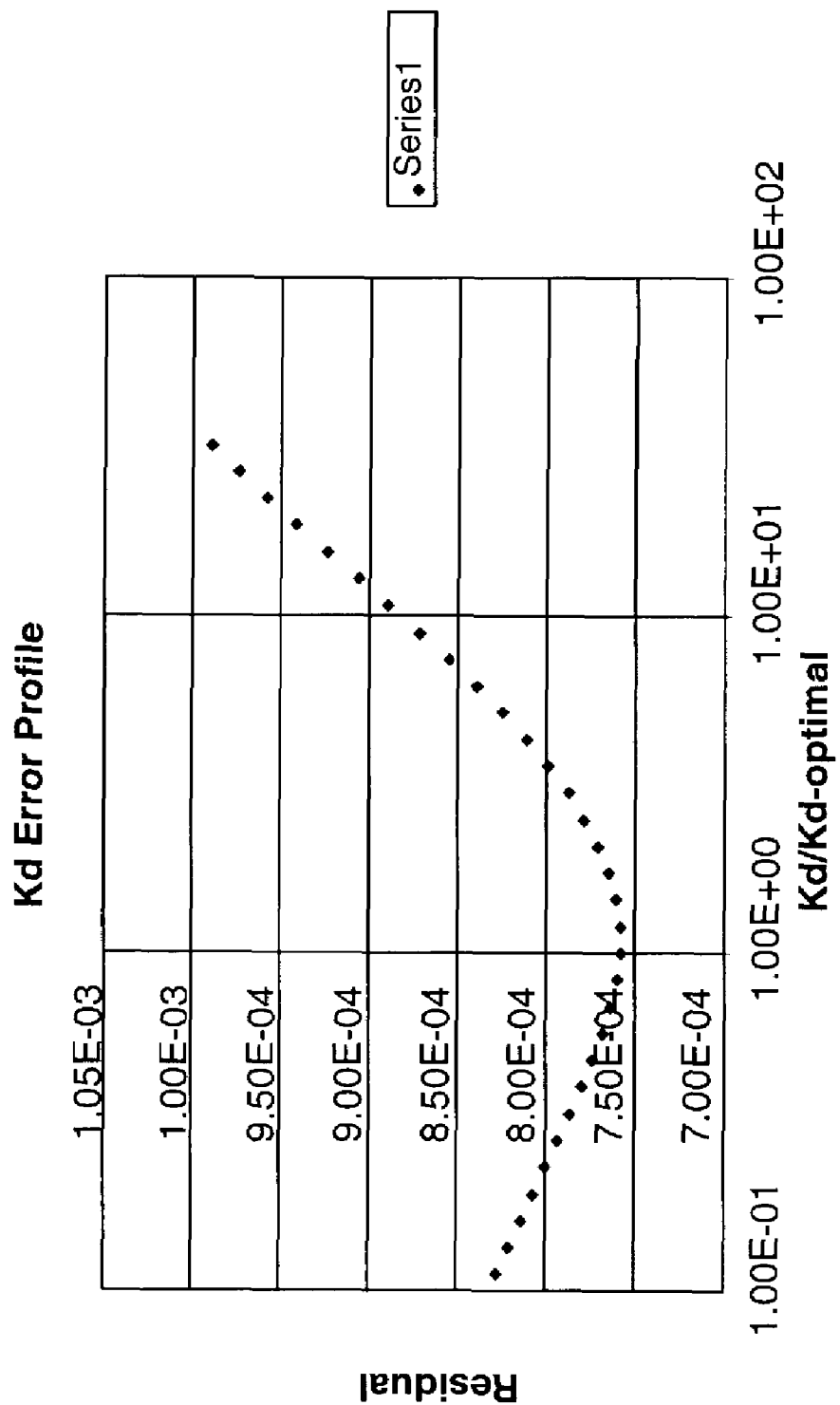
FIG. 7 depicts a hypothetical plot showing an example of an objective function for a nonlinear least squares problem applied to the determination of the value of $K_D$ for a ligand/antiligand interaction, in accordance with the present invention.

This formula defines the objective function for this nonlinear least squares problem. The problem is called a least squares problem because the objective function is the sum of the squares of the residuals (differences) between the measurements and the model predictions. The solution is the value of $K_D$ that minimizes the objective function. FIG. 7 depicts a plot showing an example of this objective function. There are many ways to minimize the objective function. Any standard function optimization algorithm, such as the steepest descent algorithm, can be used. Some objective function minimization methods take advantage of the particular structure of this objective function, for example the conjugate gradient method and the Levenberg-Marquardt method, and their use may be preferred in many instances. In this way, the strength of the ligand/antiligand bond can be quantified.

Figure 8:
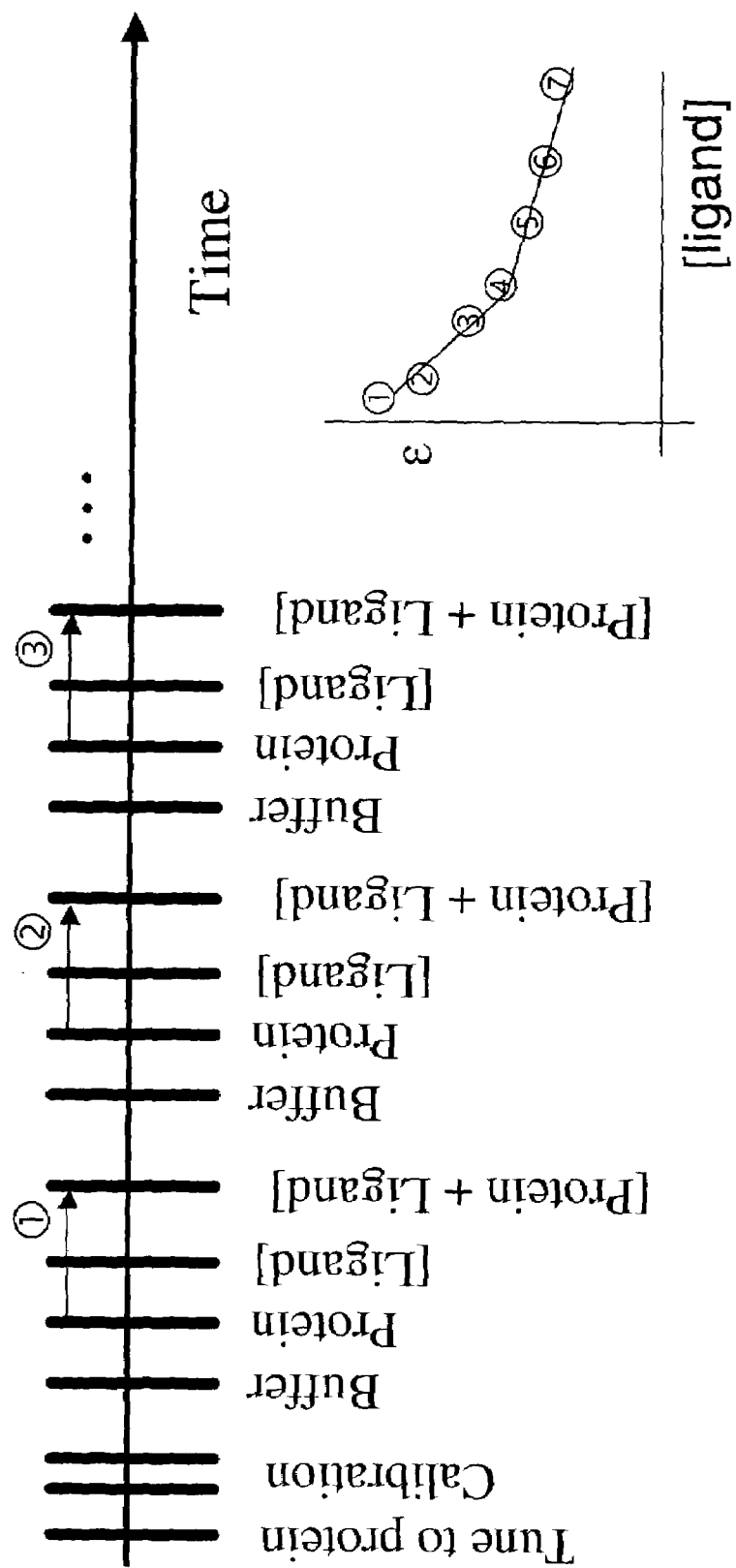
FIG. 8 provides a graphic illustration of an exemplary series of experiments that could be used to determine $K_D$, in accordance with the present invention.

In order to further illustrate the application of the nonlinear least squares analysis to the problem of determining ligand/antiligand binding strength from bulk property measurements, FIG. 8 provides an example of a series of experiments that could be used to determine $K_D$. Each line represents an experiment of the type indicated by the label adjacent to the line. Typically, an assay starts with measurements on calibrations solutions. In this particular assay, the calibrations measurements are followed by a series of sets of four experiments. Each set has the following sequence of measurements: (1) bulk property measurement of buffer alone; (2) bulk property measurement of antiligand (e.g., protein) alone in solution with buffer; (3) initial ligand concentration in solution; and (4) bulk property measurement of protein and ligand together in solution. Within each set, the two measurements involving ligand are made at the same initial concentration. The initial ligand concentration is different between sets. Usually it changes in a single direction (increases or decreases). The difference between the bulk property measurements, e.g., permittivities, of the protein alone and the protein and ligand are recorded so that a bulk property difference is obtained for each initial ligand concentration. A plot of an electromagnetically detectable bulk property ($\epsilon$) as a function of initial ligand concentration exhibits the characteristic shape of an electromagnetically detectable bulk property binding curve (such as depicted in FIGS. 2A–C and 3).

Figure 9:
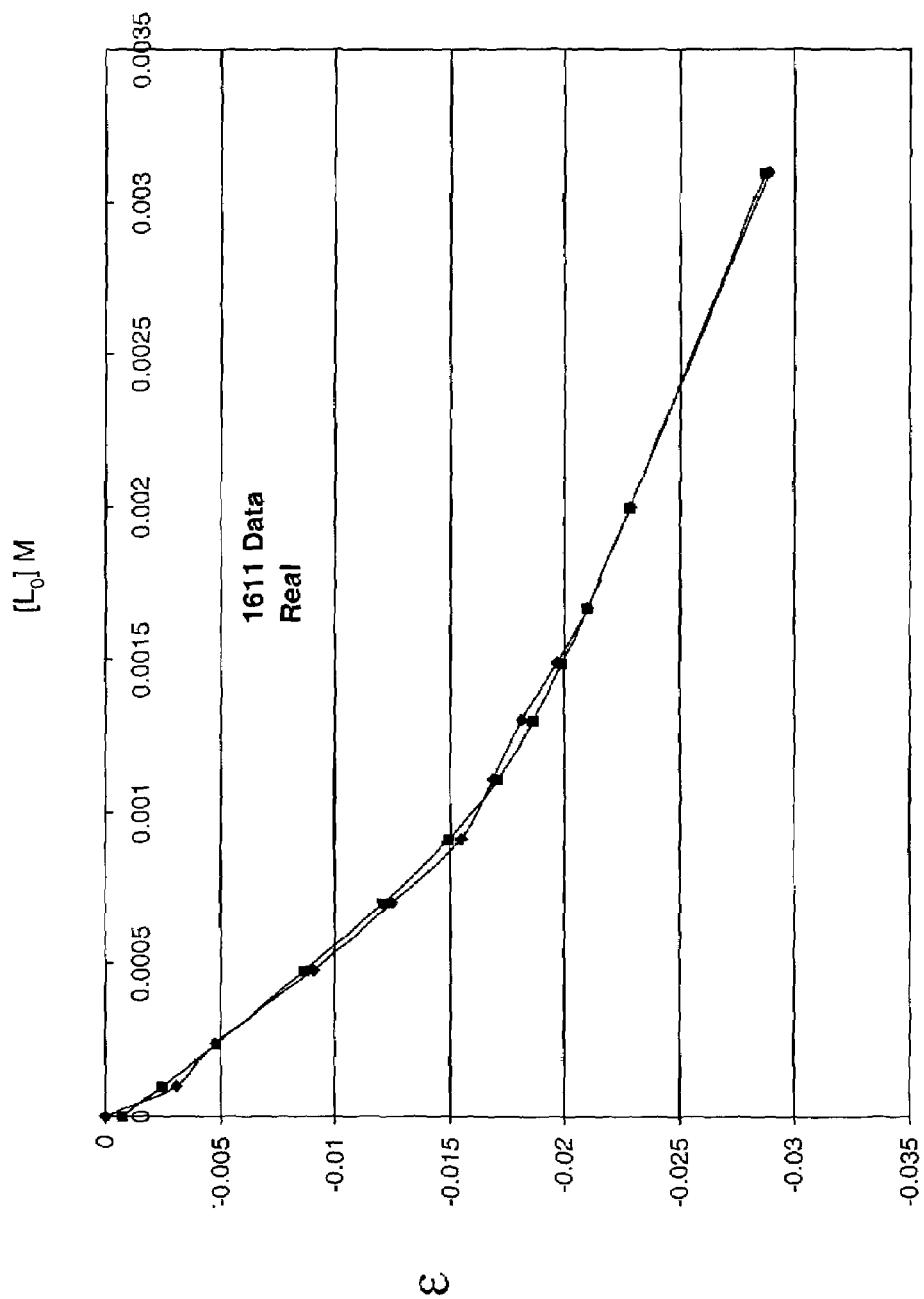
FIG. 9 shows a plot of actual measured binding data vs. nonlinear least squares fitted model data for the value of $K_D$ that produced the fit of the model to the actual data according to the nonlinear least squares technique applied in accordance with the present invention.

FIG. 9 shows a plot of permittivity relative to buffer ($\epsilon$) vs. the initial ligand concentration ($L_0$) in micromolar units for actual measured binding data (♦) and the nonlinear least squares fitted model data (■), as determined by the analysis described above. The value of $K_A$ that produced the fit of the model to the actual data is the binding affinity for the assay (i.e., the strength of the binding interaction for the particular ligand and antiligand).

C. Implementation

Various embodiments of the method of the present invention can be implemented, in whole or in part, on a computing apparatus. Useful machines for performing the operations of this invention include general-purpose digital computers or other data processing devices. Such apparatus may be specially constructed for the required purposes, or it may be a general-purpose computer selectively activated or reconfigured by a computer program stored in the computer. The processes presented herein are not inherently related to any particular computer or other apparatus. In particular, various general-purpose machines can be used with programs written in accordance with the teachings herein, or it may be more convenient to construct a more specialized apparatus to perform the required method steps. The required structure for a variety of these machines will appear from the description given above.

Certain aspects of the methods of the present invention can be embodied in computer software code. Accordingly, the present invention relates to machine-readable media that include program instructions, data, etc. for performing various operations described herein. Examples of machine-readable media include, but are not limited to, magnetic media such as hard disks, floppy disks, and magnetic tape; optical media such as CD-ROM disks; magneto-optical media such as floptical disks; and hardware devices that are specially configured to store and perform program instructions, such as read-only memory devices (ROM) and random access memory (RAM). The invention can also be embodied in a carrier wave traveling over an appropriate medium such as airwaves, optical lines, or electric lines. Examples of program instructions include both machine code, such as produced by a compiler, and files containing higher-level code that can be executed by the computer using an interpreter.

Figure 10A:
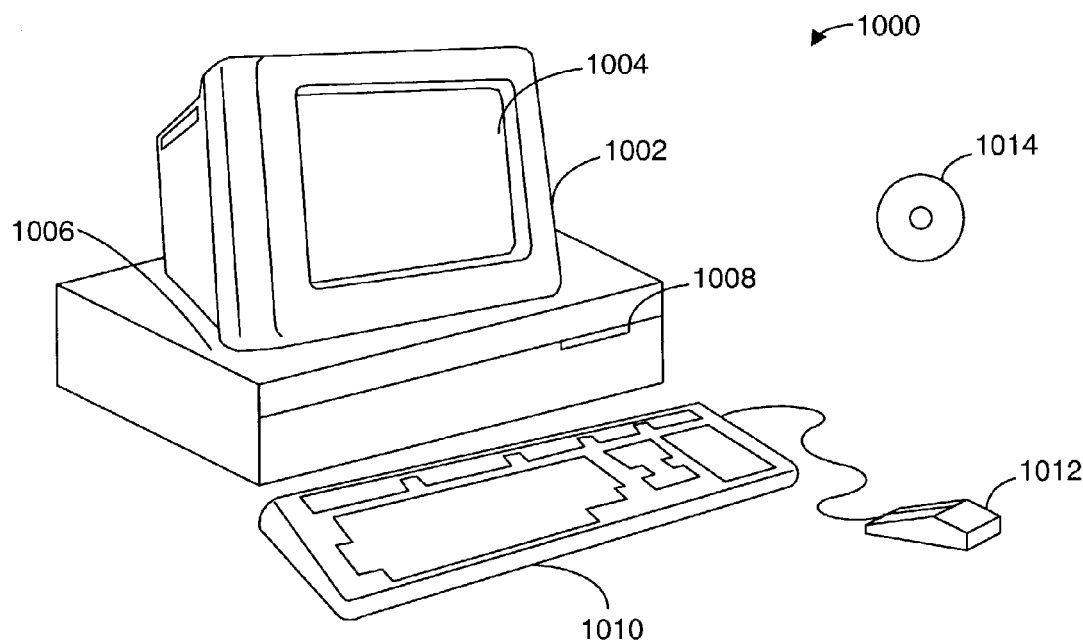
FIGS. 10A–B illustrate a computer system suitable for implementing embodiments of the present invention.

FIGS. 10A and B illustrate a computer system 1000 suitable for implementing embodiments of the present invention. FIG. 10A shows one possible physical form of the computer system. Of course, the computer system may have many physical forms ranging from an integrated circuit, a printed circuit board and a small handheld device up to a huge super computer. Computer system 1000 includes a monitor 1002, a display 1004, a housing 1006, a disk drive 1008, a keyboard 1010 and a mouse 1012. Disk 1014 is a computer-readable medium used to transfer data to and from computer system 1000.

Figure 10B:
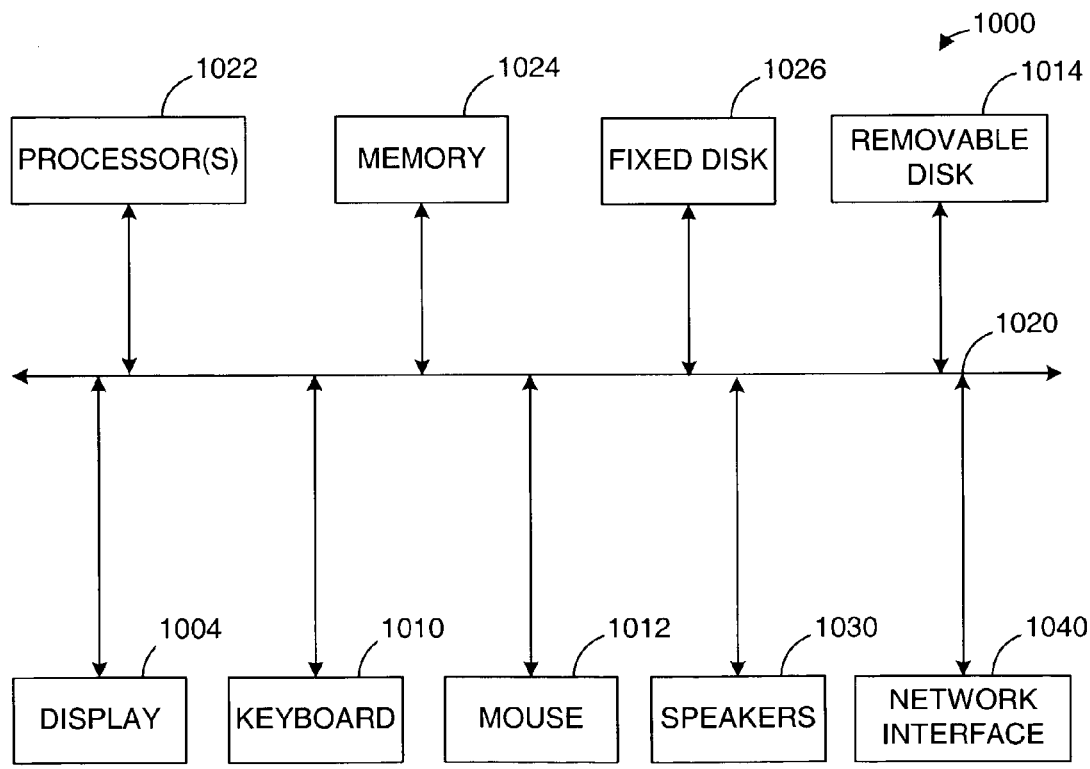

FIG. 10B is an example of a block diagram for computer system 1000. Attached to system bus 1020 are a wide variety of subsystems. Processor(s) 1022 (also referred to as central processing units, or CPUs) are coupled to storage devices including memory 1024. Memory 1024 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 1026 is also coupled bi-directionally to CPU 1022; it provides additional data storage capacity and may also include any of the computer-readable media described below. Fixed disk 1026 can be used to store programs, data and the like and is typically a secondary storage medium (such as a hard disk) that is slower than primary storage. It will be appreciated that the information retained within fixed disk 1026, may, in appropriate cases, be incorporated in standard fashion as virtual memory in memory 1024. Removable disk 1014 can take the form of any of the computer-readable media described below.

CPU 1022 is also coupled to a variety of input/output devices such as display 1004, keyboard 1010, mouse 1012 and speakers 1030. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 1022 optionally can be coupled to another computer or telecommunications network using network interface 1040. With such a network interface, it is contemplated that the CPU might receive information from the network, or might output information to the network in the course of performing the above-described method steps. Furthermore, method embodiments of the present invention may execute solely upon CPU 1022 or may execute over a network such as the Internet in conjunction with a remote CPU that shares a portion of the processing. The above-described devices and materials will be familiar to those of skill in the computer hardware and software arts.

D. EXAMPLES

The following examples provide details of experiments conducted to demonstrate ability to detect binding and determine the strength of binding of a variety of ligands to an exemplary antiligand. Ribonuclease A (RNase A) inhibitors were used as ligands, and the protein RNase A was used as the antiligand. It should be understood the following is representative only, and that the invention is not limited by the details set forth in these examples.

Example 1

The following example provides details concerning experiments conducted to determine the binding ability and strength of binding of cytidine 2'-monophosphate free acid (2'-CMP), cytidine 3'-monophosphate free acid (3'-CMP) and cytidine 5'-monophosphate free acid (5'-CMP) to the protein Ribonuclease A (RNase A). The results of the binding assays are presented in a variety of graphical formats to illustrate that the invention is not limited to any particular data presentation format. The binding equilibrium (dissociation) constants ($K_D$) for ligands that bind to the antiligand were also determined in accordance with the techniques described herein.

Materials. Ribonuclease A, (RNase A, catalogue # R5503)), cytidine 2'-monophosphate free acid (2'-CMP, catalogue # C7137), cytidine 3'-monophosphate free acid (3'-CMP, catalogue # C1133), cytidine 5'-monophosphate free acid (5'-CMP, catalogue # C1131), sodium chloride (catalogue # S7653), magnesium chloride (catalogue # M2670), Bis-Tris free base (catalogue # B7535), and Bis-Tris hydrochloride salt (catalogue # B6032) were purchased from Sigma (St. Louis, Mo.). The surfactant NP-40 (catalogue # 492015) was purchased from Calbiochem (San Diego, Calif.). These reagents were used without further purification. All solutions were prepared using milliQ water. These experiments were performed in a pH 6.0 150 mM BIS-TRIS buffer containing 10 mM sodium chloride, 10 mM magnesium chloride, and 0.005% v/v NP-40.

Preparation of Sample Solutions. The protein solution was prepared by dissolving RNase A in the Bis-Tris buffer to give a final concentration of 1 mM protein; no subsequent dialysis was performed. The ligand solutions were prepared by dissolving 2'-CMP, 3'-CMP or 5'-CMP in the 1 mM RNase A solution to give a final concentration of 4 mM ligand. A series of samples which formed the basis of the ligand binding curve were prepared by mixing various ratios of the above two solutions as outlined in Table 1.

Multipole Coupling Spectroscopy (MCS). The MCS system used to collect these data consisted of: (1) a co-axial resonating detector operating at 1.3 GHz, (2) a 8719ET network analyzer from Agilent Technologies, (Santa Rosa, Calif.), (3) an automated fluidic module (AFM) for drawing samples into the flow cell, which was composed of a Cavro XP 3000 digital pump and a Cavro smart valve (6 port) from Tecan (Santa Clara, Calif.), (4a) a thermal enclosure based on a zero gradient oven design which houses both the detector and sample flow cell, (4b) a high resolution thermal controller (PID) and (5) a PC computer running LabVIEW™ software from National Instruments Corporation (Austin, Tex.) to communicate between all these components. The flow cell (a polyimide tube with an 0.0285" I.D. and an 0.0305" O.D. from HV Technologies, Trenton, Ga.) was mounted on the top of the coaxial resonating detector such that only the wall of the tubing separated the detector and the fluidic sample. The AFM was used to draw the fluidic samples into the detection region of the flow cell. The network analyzer settings used were $S_{11}$ reflection, log magnitude, linear frequency sweep in stepped mode, 401 points, IF bandwidth of 30 Hz, power of −5 dBm, and no cable calibration was applied.

To set up the instrument to measure the data of a binding titration, the protein solution was first introduced to the flow cell of the coaxial resonating fixture and the fixture was coupled by adjusting the size of the gap until the desired reflection was achieved (approximately −30 dBm). The co-axial resonator has a sliding mechanism composed of a single dimension translation stage and a mechanical motor (Picomotor Driver from New Focus Inc., San Jose, Calif.) to adjust the gap size separating the pieces of coax such that the desired MCS reflection is achieved. Each of the remaining fluidic samples described in Table 1, below, were sequentially measured. The thermal enclosure contains two fluidic samples in series at any one time; while the latter sample is coming to thermal equilibrium, the former fluidic sample is in the detector region where its MCS properties are recorded using the LabVIEW™ software. After recording the MCS data for the biological samples, the MCS data for three or more well characterized calibration solutions were measured using the protocol described above. An algorithm, known as bilinear least-squares calibration (for example, as described in Folgero, Meas. Sci. Technol. 7 (1996) 1260–1269), uses the MCS data measured for the calibration solutions to calculate the permittivity values from the MCS data of the fluid samples.

TABLE 1

|  | µL of Ligand Solution | µL of Protein Solution | [Ligand] mM | [RNase] mM |
|---|---|---|---|---|
| Replicate protein runs 1 | 0 | 200 | 0 | 1.0 |
| Replicate protein runs 2 | 0 | 200 | 0 | 1.0 |
| Replicate protein runs 3 | 0 | 200 | 0 | 1.0 |
| Replicate protein runs 4 | 0 | 200 | 0 | 1.0 |
| 5 | 6.00 | 200 | 0.117 | 1.0 |
| 6 | 12.50 | 200 | 0.235 | 1.0 |
| 7 | 19.00 | 200 | 0.347 | 1.0 |
| 8 | 26.00 | 200 | 0.460 | 1.0 |
| 9 | 33.50 | 200 | 0.574 | 1.0 |
| 10 | 42.00 | 200 | 0.694 | 1.0 |
| 11 | 51.00 | 200 | 0.813 | 1.0 |
| 12 | 60.50 | 200 | 0.929 | 1.0 |
| 13 | 70.50 | 200 | 1.043 | 1.0 |
| 14 | 82.00 | 200 | 1.163 | 1.0 |
| 15 | 94.00 | 200 | 1.279 | 1.0 |
| 16 | 107.00 | 200 | 1.394 | 1.0 |
| 17 | 155.00 | 200 | 1.746 | 1.0 |
| 18 | 110.00 | 100 | 2.095 | 1.0 |
| 19 | 158.00 | 100 | 2.450 | 1.0 |
| 20 | 116.00 | 50 | 2.795 | 1.0 |
| 21 | 185.00 | 50 | 3.149 | 1.0 |
| 22 | 200.00 | 0 | 4.000 | 1.0 |
| Replicate protein runs 23 | 0 | 200 | 0 | 1.0 |
| Replicate protein runs 24 | 0 | 200 | 0 | 1.0 |
| Replicate protein runs 25 | 0 | 200 | 0 | 1.0 |
| Replicate protein runs 26 | 0 | 200 | 0 | 1.0 |

FIGS. 11A–G show data from this experiment, plotted in various formats.

Figure 11A:
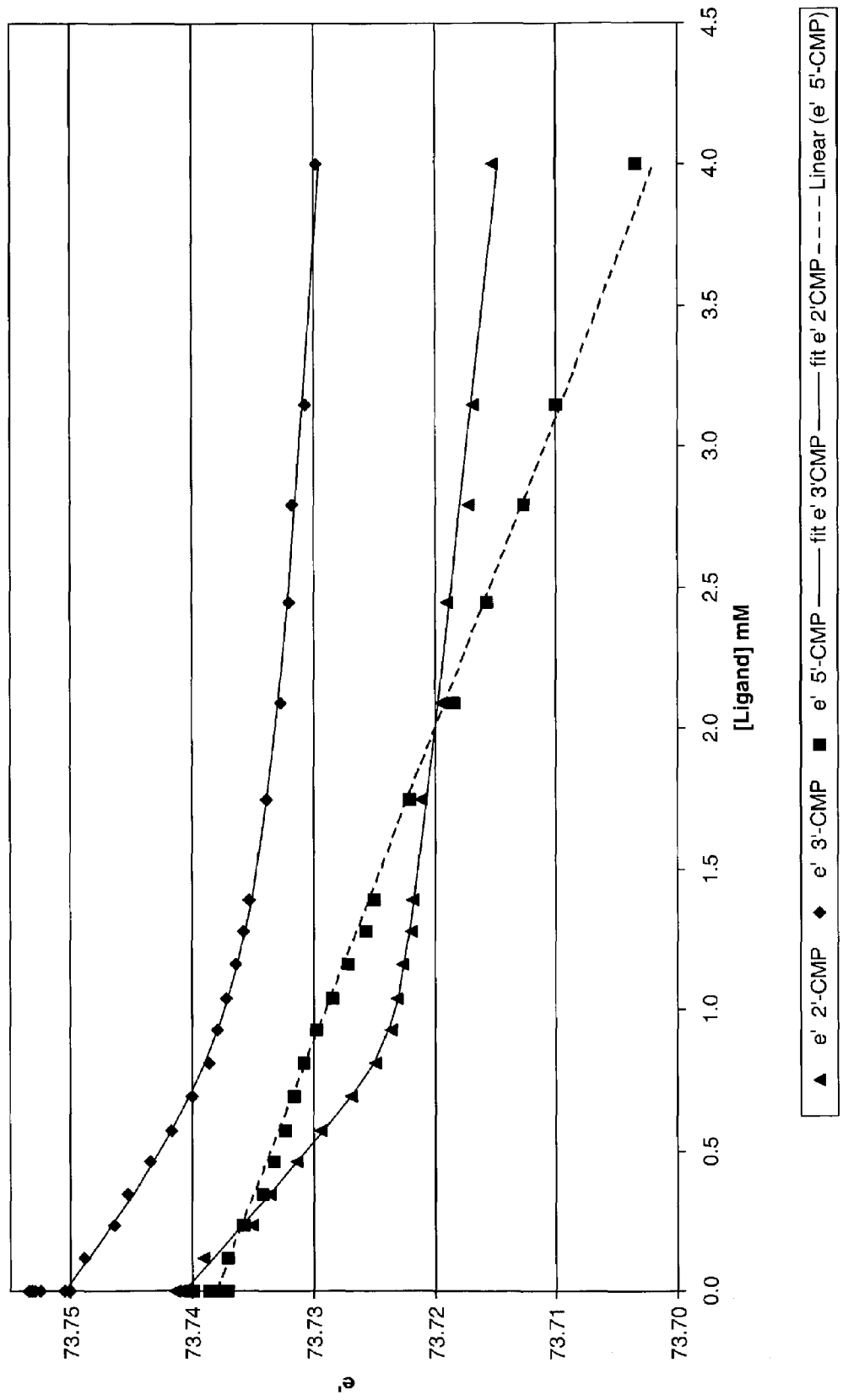
FIGS. 11A–G show data from an experiment that illustrates advantages of the present invention plotted in various formats.

FIG. 11A shows the absolute permittivity values (e' real part of permittivity) for RNase A accompanying its binding to the either 2'-CMP (triangles), 3'-CMP (diamonds), or 5'-CMP (squares) at various ligand concentrations at 27° C. The experimental data was fitted using the bilinear least-squares algorithm described above to determine the $K_D$ values for the protein:ligand interaction (solid lines): 2'-CMP ($K_D$=10 µM), 3'-CMP ($K_D$=130 µM). No suitable curve fit was achieved for the 5'-CMP data due to it weak affinity for RNase A (a linear regression of the experimental data is shown as a dashed line).

Figure 11B:
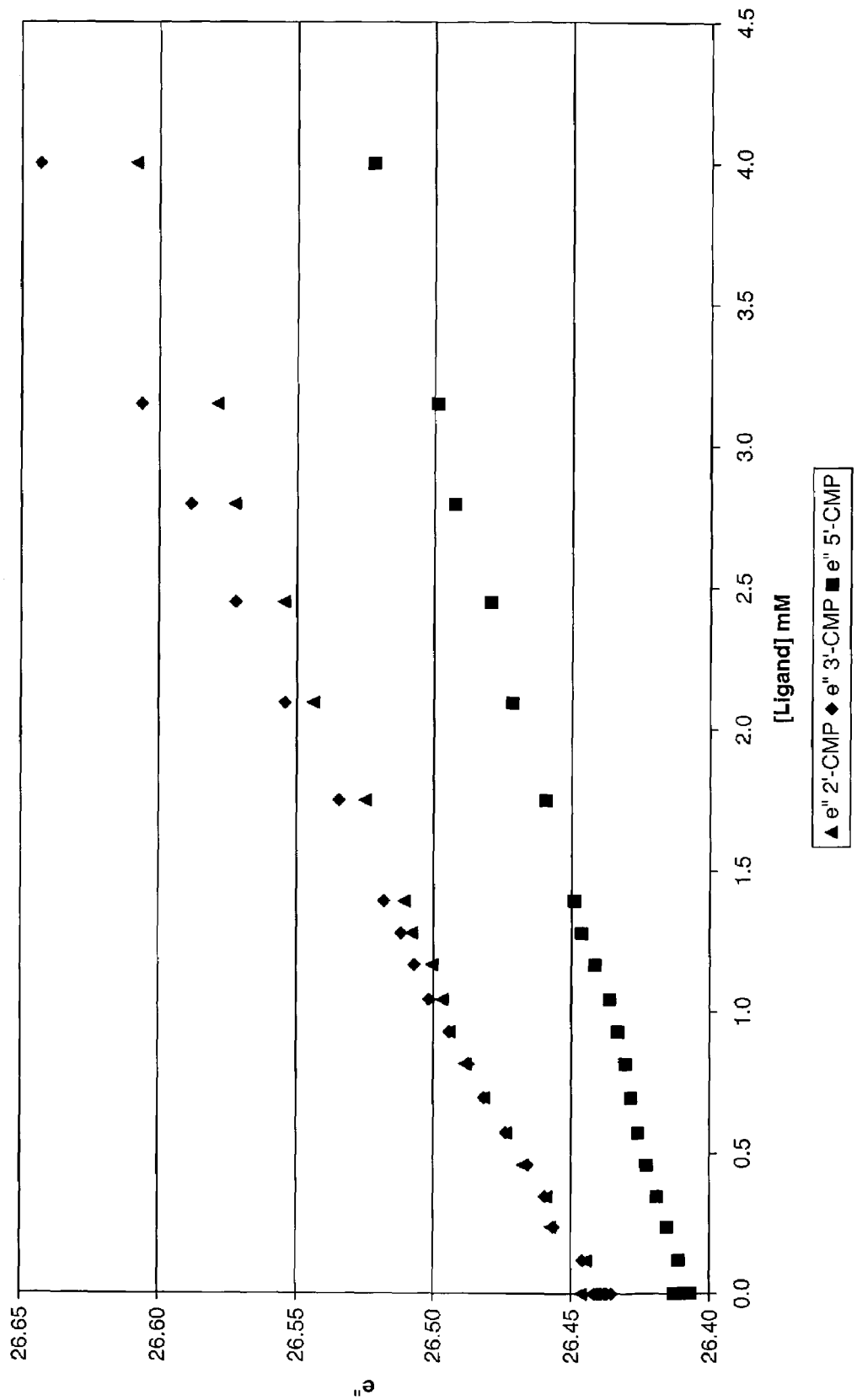

FIG. 11B shows the absolute permittivity values (e" imaginary part of permittivity) for RNase A accompanying its binding to the either 2'-CMP (triangles), 3'-CMP (diamonds), or 5'-CMP (squares) at various ligand concentrations at 27° C.

Figure 11C:
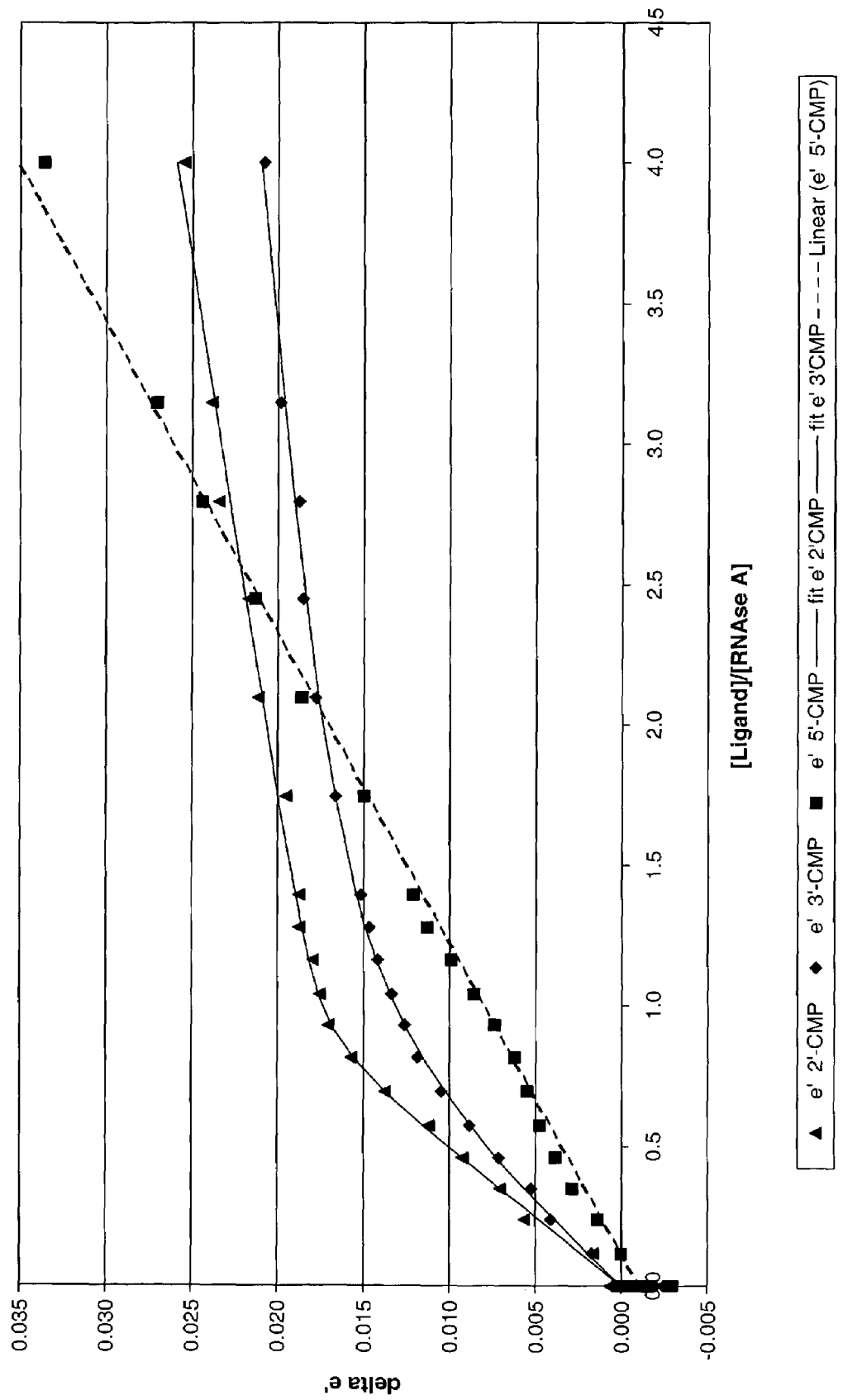

FIG. 11C shows the change in the permittivity (e' real part of permittivity) for RNase A accompanying its binding to the either 2'-CMP (triangles), 3'-CMP (diamonds), or 5'-CMP (squares) at various ligand-to-protein rations at 27° C. The experimental data is fitted using an algorithm to determine the $K_D$ values for the protein:ligand interaction (solid lines): 2'-CMP ($K_D$=10 μM), 3'-CMP ($K_D$=130 μM). No suitable curve fit was achieved for the 5'-CMP data due to it weak affinity for RNase A (a linear regression of the experimental data is shown as a dashed line).

Figure 11D:
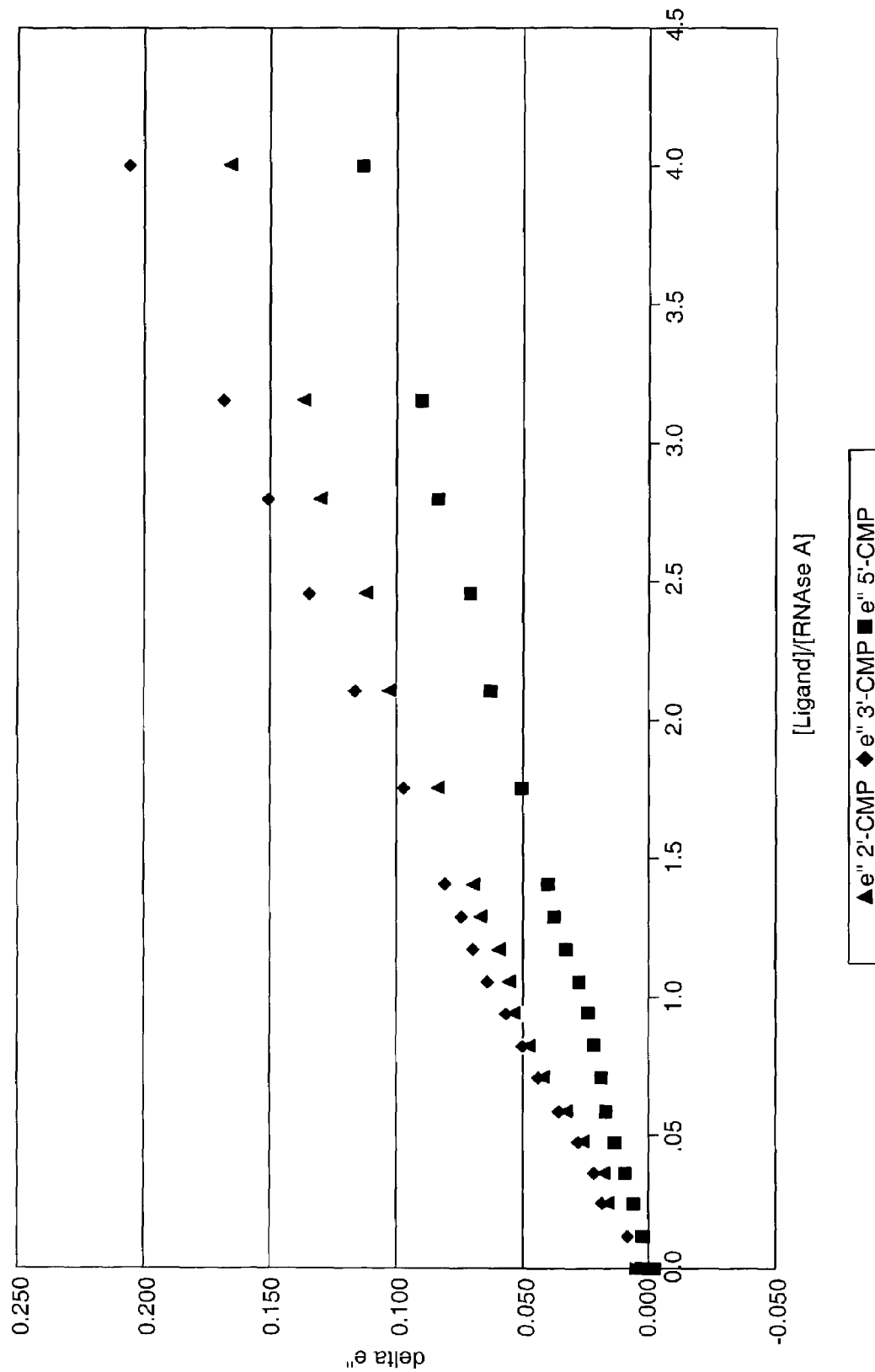

FIG. 11D shows the change in the permittivity (e" imaginary part of permittivity) for RNase A accompanying its binding to the either 2'-CMP (triangles), 3'-CMP (diamonds), or 5'-CMP (squares) at various ligand-to-protein rations at 27° C.

Figure 11E:
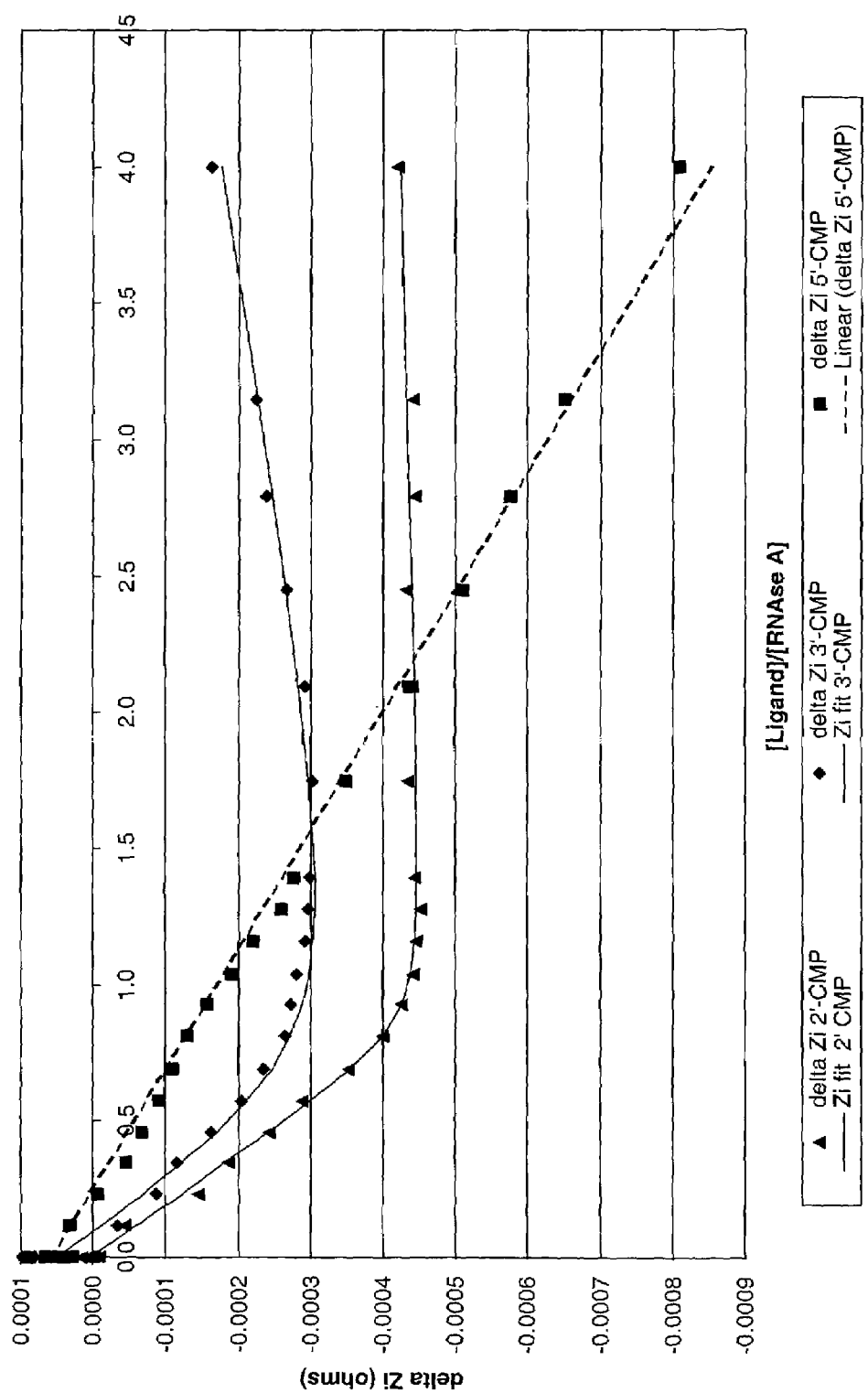

FIG. 11E shows the change in the impedance (Zi, imaginary part of impedance) for RNase A accompanying its binding to the either 2'-CMP (triangles), 3'-CMP (diamonds), or 5'-CMP (squares) at various ligand-to-protein rations at 27° C. The experimental data is fitted using an algorithm to determine the $K_D$ values for the protein:ligand interaction (solid lines): 2'-CMP ($K_D$=11 μM), 3'-CMP ($K_D$=75 μM). No suitable curve fit was achieved for the 5'-CMP data due to it weak affinity for RNase A (a linear regression of the experimental data is shown as a dashed line).

Figure 11F:
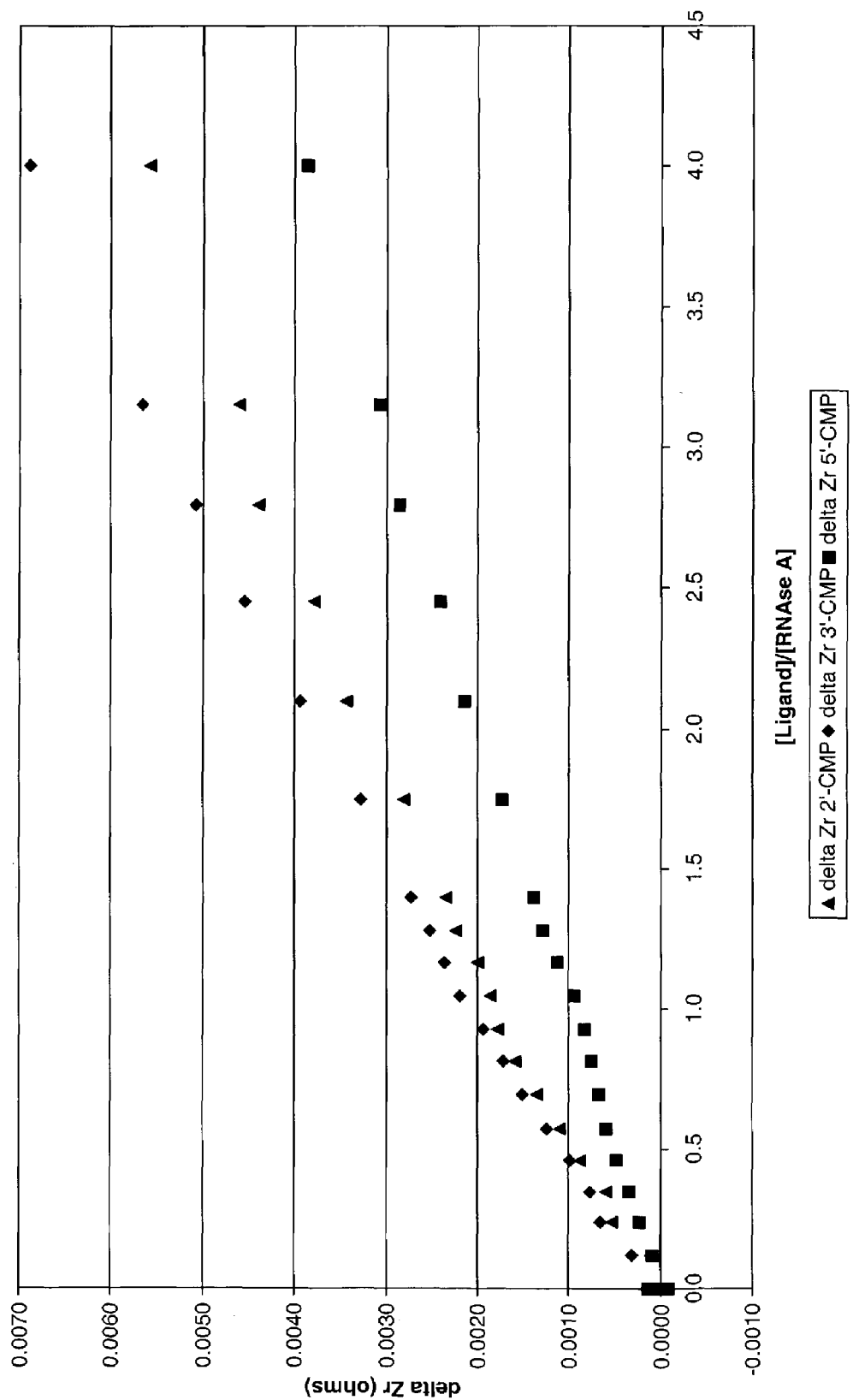

FIG. 11F shows the change in the impedance (Zr, real part of impedance) for RNase A accompanying its binding to the either 2'-CMP (triangles), 3'-CMP (diamonds), or 5'-CMP (squares) at various ligand-to-protein rations at 27° C.

Figure 11G:
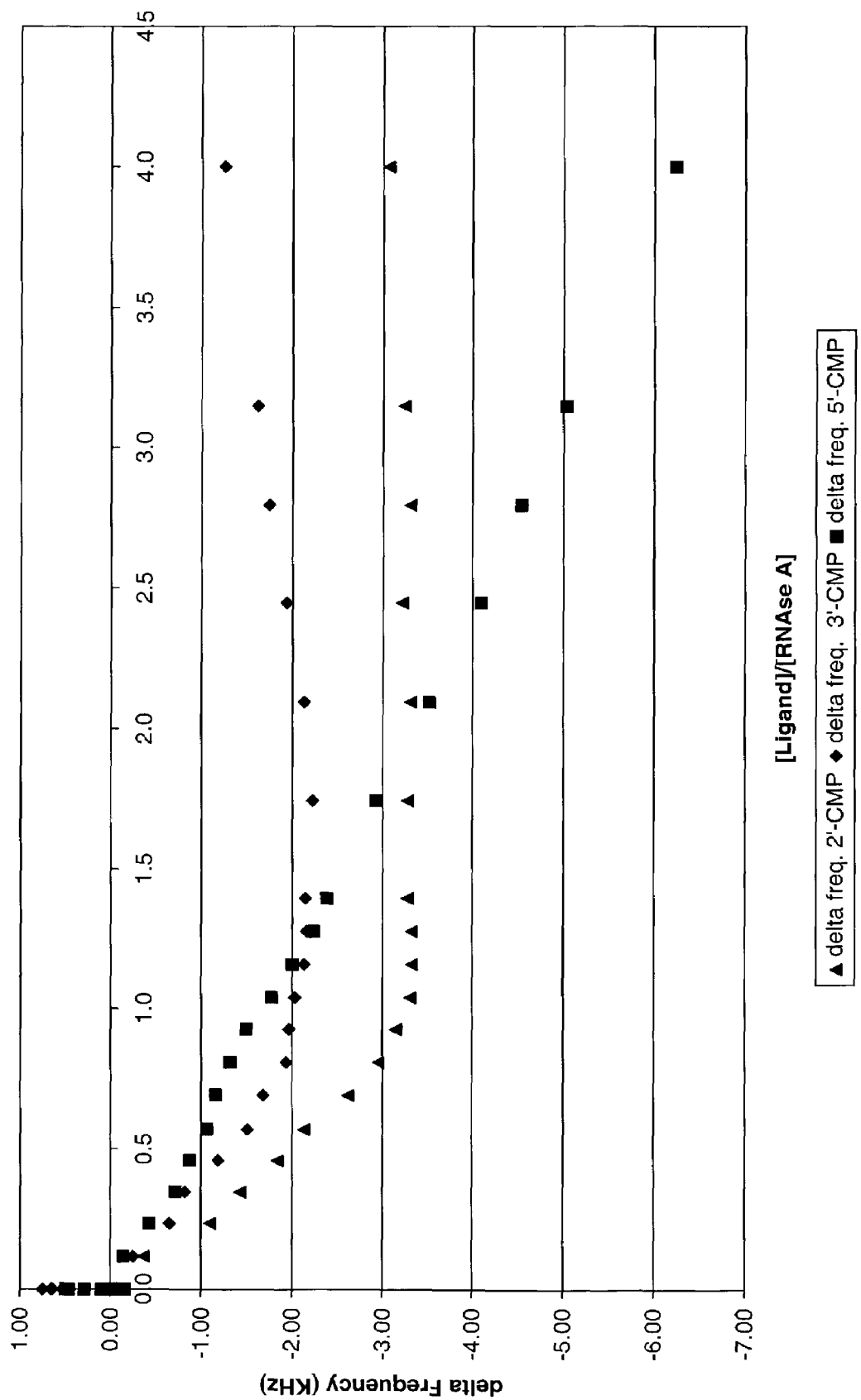

FIG. 11G shows the change in the frequency for RNase A accompanying its binding to the either 2'-CMP (triangles), 3'-CMP (diamonds), or 5'-CMP (squares) at various ligand-to-protein rations at 27° C.

Table 2, below, provides the chemical structure of each of the three CMP ligands used in this experiment and a comparison of their dissociation constants ($K_D$) binding to RNase as determined by Isothermal Titration Calorimetry (ITC) and Multipole Coupling Spectroscopy (MCS). The results show that 2'-CMP is a relatively strong binder to RNase A, while 3'-CMP is a relatively weak binder to RNase A. The binding of 5'-CMP to RNase A is unmeasurably weak, thus giving non-binding results for both ITC and MCS.

TABLE 2

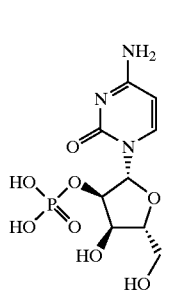

| | ▲ 2'-CMP | ♦ 3'-CMP | ■ 5'-CMP |
|---|---|---|---|
| ITC $K_D$ | 6.3 μM | 75 μM | N.A.[1] |
| MCS $K_D$[2] | 10 μM | 130 μM | N.A.[1] |

[1]Not applicable (N.A.).
[2]$K_D$ values determined for the fitted experimental data shown in FIG. 11C.

Example 2

As verification of the generality of the inventive technique in bulk property situations other than the measurements involving permittivity, an experiment was carried out by measuring refractive index as the bulk property of a test solution. The binding assay used was one of the ones shown in Example 1, namely binding of RNase A to the RNase inhibitor 2'CMP. The refractometer used to measure the refractive index of the samples was a Wyatt Technologies Optilab DSP refractometer, calibrated using sodium chloride solutions as described in the manufacturer's instructions. RNase (Sigma) was dissolved in a buffer containing 150 mM Bis-Tris, 10 mM NaCl, 10 mM $MgCl_2$, 0.005% $NaPO_4$, pH 6, to provide 1 mM RNase. A portion of this solution was fed into the reference cell of the refractometer, and the instrument was left standing until the readout had stabilized. The test ligand, 2'CMP, was dissolved to 4 mM in a portion of the 1 mM RNase solution, and a titration was prepared to produce the following concentrations.

TABLE 3

| Sample # | μL of 4 mM 2'CMP (in 1 mM RNase) added to 1.5 mL of 1 mM RNase | final concentration of 2'CMP in mM |
|---|---|---|
| 1 | 45 | 0.120 |
| 2 | 90 | 0.233 |
| 3 | 180 | 0.441 |
| 4 | 270 | 0.628 |
| 5 | 360 | 0.797 |
| 6 | 405 | 0.876 |
| 7 | 450 | 0.951 |
| 8 | 495 | 1.022 |
| 9 | 540 | 1.091 |
| 10 | 600 | 1.177 |
| 11 | 675 | 1.279 |
| 12 | 900 | 1.545 |
| 13 | 1500 | 2.060 |
| 14 | 0 | 4.120 |

Samples were then loaded into the Optilab sample cell using a syringe and measured in the following order:
Sample
1 mM RNase
1 mM RNase
3
4
5
6
RNase alone
7
8
9
10
RNase alone
11
12
13

Figure 12:
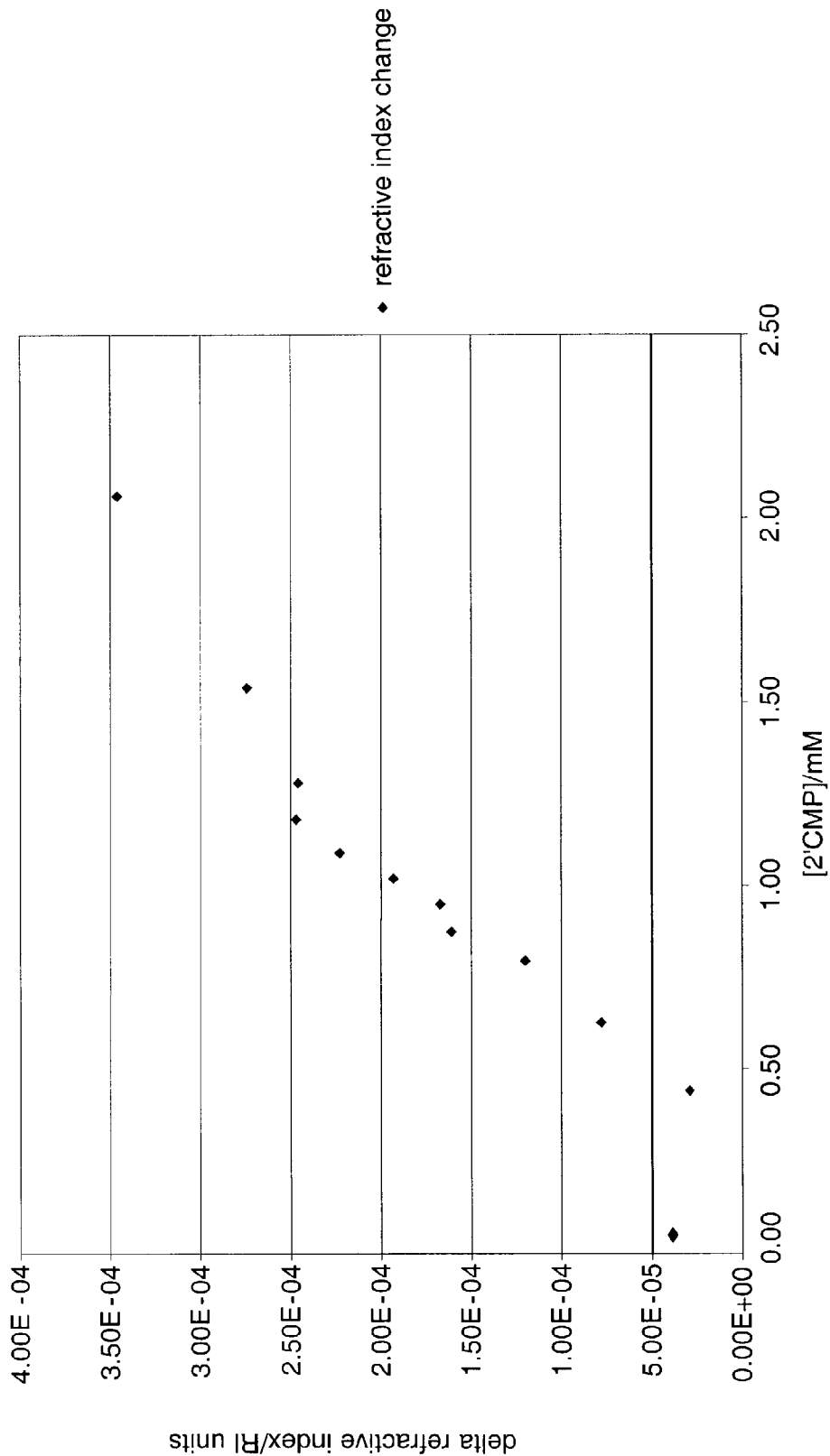
FIG. 12 shows a plot of change in refractive index with change in concentration of 2'-CMP, as a demonstration of bind of 2'-CMP to RNase A using refractive index as a measurable bulk property.

The refractometer was zeroed using a 1 mM RNase solution. Data from the Optilab refractometer was processed using the DNDC software supplied with the instrument by Wyatt Technologies. The refractive index change relative to the reference cell was calculated using the software and plotted against the concentration of 2'CMP. The plot (FIG. 12) deviates significantly from linearity, indicating that binding has taken place. No attempt was made to calculate an equilibrium constant from this data.

The following commonly owned; co-pending patents and applications are herein incorporated by reference in their entirety for all purposes, primarily to serve as background information for those not currently familiar with MCS technology:

U.S. Pat. No. 6,368,795;
U.S. Pat. No. 6,338,968;
U.S. Pat. No. 6,395,480;
U.S. Pat. No. 6;376,258;
Ser. No. 09/365,978 entitled "Test Systems and Sensors for Detecting Molecular Binding Events," filed Aug. 2, 1999. now U.S. Pat. No. 6.485. 905. issued under the amended title "Bio-Assay Device";
U.S. Pat. No. 6,287,776;
U.S. Pat. No. 6,340,568;
U.S. Pat. No. 6,287,874;
Ser. No. 09/923,474 entitled "Methods for analyzing protein binding events" filed Aug. 6, 2001;
Ser. No. 09/687,456 entitled "System and method for detecting and identifying molecular events in a test sample," filed Oct. 13, 2000;
Ser. No. 09/775,718 entitled "Bioassay device for detecting molecular events," filed Feb. 1, 2001;
Ser. No. 09/775,710 entitled "System and method for detecting and identifying molecular events in a test sample using a resonant test structure," filed Feb. 1, 2001;
Ser. No 09/837,898 entitled "Method and Apparatus for Detection of Molecular Events Using Temperature Control of Detection Environment," filed Apr. 18, 2001;
Ser. No. 09/880,331 entitled "Reentrant Cavity Bioassay for Detecting Molecular or Cellular Events," filed Jun. 12, 2001;
Ser. No. 09/880,746 entitled "Pipette-Loaded Bioassay Assembly for Detecting Molecular or Cellular Events," filed Jun. 12, 2001. now U.S. Pat. No. 6,461,808;
Ser. No. 09/929,513 entitled "Method for analyzing cellular events," filed Aug. 13, 2001;
Ser. No. 09/929,520 entitled "Well-based biosensors for detecting molecular or cellular events," filed Aug. 13, 2001;
Ser. No. 09/929,521 entitled "Coplanar waveguide biosensor for detecting molecular or cellular events," filed Aug. 13, 2001;
Ser. No. 09/972,306 entitled "System and method for creating a solution with desired dielectric properties useful for determining the complex permittivity of a test solution," filed Oct. 5, 2001;
Ser. No. 09/976,628 entitled "Repuncturable self sealing sample container with internal collapsible bag," filed Oct. 12, 2001; and
Ser. No. 10/073,827 entitled "A system and method for characterizing the permittivity of molecular events," filed Feb. 11, 2002.

Conclusion

The present invention novel methods and products for analyzing molecular binding events in which the formation of any ligand/antiligand complexes can be directly detected in a mixture (e.g., a solution) without requiring separation of the components of the mixture from each other. The invention provides methods for detecting binding between ligands and antiligands, utilizing a technique that is capable of elucidating ligand/antiligand binding from electromagnetically detectable bulk property measurements of a mixture of the ligand and antiligand. Using this technique, it is possible to screen libraries without the need for labeling of either the target antiligand or ligand. The invention also provides a method for determining the strength of ligand/antiligand binding.

Although the foregoing invention has been described in some detail for purposes of clarity of understanding, it will be apparent that certain changes and modifications can be practiced within the scope of the appended claims. It should be noted that there are alternative ways of implementing both the methods and systems of the present invention. For instance, while the invention is in part described with reference to electromagnetic signals in the microwave range used to obtain permittivity measurements of solutions, other regions of the electromagnetic spectrum can be used to obtain other bulk property measurement signals from solutions, and those measurements can be processed to decipher binding information in accordance with the present invention. Accordingly, the present embodiments are to be considered as illustrative and not restrictive, and the invention is not to be limited to the details given herein, but may be modified within the scope and equivalents of the appended claims.

What is claimed is:

1. A method of detecting ligand/antiligand binding, comprising:
   obtaining measurements of an electiomagnetically detectable bulk property of a mixture containing a ligand and an antiligand for each of a plurality of initial ligand concentrations, wherein (1) said bulk property is a measurable property of said mixture that is affected by more than one and up to all individual components of said mixture and (2) said measurement is made (a) without separation of said ligand or said antiligand from other components of said mixture and (b) without use of a signal that is selective for only said ligand, said antiligand, or a binding complex of said ligand and said antiligand;
   processing a plurality of the obtained bulk property measurements and corresponding initial ligand concentrations to determine a relationship between the bulk property measurements of the mixture and the initial ligand concentrations as initial ligand concentration changes; and
   determining the formation or absence of a ligand/antiligand complex based on the relationship.

2. The method of claim 1, wherein said electromagnetically detectable bulk property is selected from the group consisting of permittivity, susceptibility, index of refraction and absorbance.

3. The method of claim 1, wherein said electromagnetically detectable bulk property measurements are represented by electromagnetic signals.

4. The method of claim 1, wherein the relationship is linear, and the linear relationship indicates the absence of a ligand/antiligand complex.

5. The method of claim 1, wherein the relationship is nonlinear, and the nonlinear relationship indicates the formation of a ligand/antiligand complex.

6. The method of claim 1, wherein the processing comprises plotting the bulk property measurements vs. the initial ligand concentrations.

7. The method of claim 5, further comprising quantifying the strength of the ligand/antiligand complex by computing an equilibrium constant for the ligand, antiligand and complex in the mixture.

8. The method of claim 7, wherein said computation comprises a nonlinear least squares analysis.

9. The method of claim 1, wherein said method is implemented using a computing apparatus.

10. The method of claim 1, wherein said ligand and antiligand are unlabelled.

11. The method of claim 10, wherein said antiligand is a protein.

12. The method of claim 11, wherein said antiligand is a known drug-target receptor protein and said ligand binds to said receptor protein.

13. The method of claim 12, wherein said ligand is selected from the group consisting of peptides, oligosaccharides, nucleic acids, lipids, antibodies and fragments thereof, steroids, members of drug candidate libraries of compounds, and cells.

14. A method of screening ligands for those having binding affinity for an antiligand target of interest, comprising:

conducting the method of claim 1 for a plurality of ligands.

* * * * *